(12) United States Patent
Horn et al.

(10) Patent No.: US 7,672,791 B2
(45) Date of Patent: Mar. 2, 2010

(54) METHOD OF PERFORMING THREE-DIMENSIONAL MOLECULAR SUPERPOSITION AND SIMILARITY SEARCHES IN DATABASES OF FLEXIBLE MOLECULES

(75) Inventors: Hans Werner Horn, San Jose, CA (US); Andreas Kraemer, Cupertino, CA (US); Julia Elizabeth Rice, Sunnyvale, CA (US)

(73) Assignee: International Business Machines Corporation, Armonk, NY (US)

( * ) Notice: Subject to any disclaimer, the term of this patent is extended or adjusted under 35 U.S.C. 154(b) by 566 days.

(21) Appl. No.: 10/462,056

(22) Filed: Jun. 13, 2003

(65) Prior Publication Data

US 2004/0254735 A1 Dec. 16, 2004

(51) Int. Cl.
*G06F 17/00* (2006.01)
*G06G 7/58* (2006.01)

(52) U.S. Cl. .............. 702/27; 702/19; 702/22; 703/11; 703/12

(58) Field of Classification Search ............ None
See application file for complete search history.

(56) References Cited

U.S. PATENT DOCUMENTS

| | | | |
|---|---|---|---|
| 5,510,240 A | 4/1996 | Lam et al. | |
| 5,752,019 A | 5/1998 | Rigoutsos et al. | |
| 5,787,279 A | 7/1998 | Rigoutsos | |
| 6,346,290 B1 | 2/2002 | Schultz et al. | |
| 6,376,253 B1 | 4/2002 | Anderson, III et al. | |
| 6,395,480 B1 | 5/2002 | Hefti | |
| 6,399,389 B1 | 6/2002 | Parce et al. | |
| 6,410,331 B1 | 6/2002 | Schultz et al. | |
| 6,420,179 B1 | 7/2002 | Schultz et al. | |
| 6,485,905 B2 | 11/2002 | Hefti | |
| 2003/0215877 A1* | 11/2003 | Love et al. | 435/7.1 |

FOREIGN PATENT DOCUMENTS

WO WO 92/01933 A1 2/1992

OTHER PUBLICATIONS

Kuntz. Structure-Based Strategies for Drug Design and Discovery. Science, vol. 257, Aug. 1992, pp. 1078-1082.*
Definition of Hydrogen Bond, Biotech Life Sciences Dictionary at biotech.icmb.utexas.edu Accessed Jun. 26, 2006.*
Martin et al. A fast new approach to pharmacophore mapping and its application to dopaminergic and benzodiazepine agonists. Journal of Computer-Aided Molecular Design, vol. 7, 1993, pp. 83-102.*
McMartin et al. Flexible matching of test ligands to a 3D pharmacophore using a molecular superposition force field: Comparision of predicted and experimental conformation of inhibitors of three enzymes. Journal of Computer-Aided Molecular Design, vol. 9, 1995, pp. 237-250.*
Dowd et al. MM3(92) Analysis of Inositol Ring Puckers. Australian Journal of Chemistry, 1996, vol. 49, pp. 327-335.*
Cremer et al. A general definition of ring puckering coordinates. Journal of the American Chemical Society. vol. 97, 1975, pp. 1354-1358.*
Levitt et al. Aromatic rings act as hydrogen bond acceptors. Journal of Molecular Biology. 1988, vol. 201, pp. 751-754.*
Atta-ur-Raman. Nuclear Magnetic Resonance: Basic Principles. New York: Springer-Verlag. 1986, pp. 69-79.*
Kemp et al. Organic Chemistry. New York: Worth Publishers, Inc. 1980, pp. 24-26 and 312-314.*
Liang et al. Ab initio studies of lipid model species. 2. Conformational analysis of inositols. Journal of the American Chemical Society, 1994, vol. 116, pp. 3904-3911.*
Baptista et al. Simulation of protein conformational freedom as a function of pH: Constant-pH molecular dynamics using implicit titration. Proteins: Structure, Function and Genetics, vol. 27, 1997, pp. 523-544.*
Brooks et al. CHARMM: A program of macromolecular energy, minimization, and dynamics calculations. Journal of Computational Chemistry, vol. 4, 1983, pp. 187-217.*
Eisenberg et al. The helical hydrophobic moment: a measure of the amphiphilicity of a helix. Nature, vol. 299, 1982, pp. 371-374.*
Hendsch et al. Do salt bridges stabilize proteins? A continuum electrostatic analysis. Protein Science, 1994, vol. 3, pp. 211-226.*
Creighton et al. Sequences of the genes and polypeptide precursors for two bovine protease inhibitors. Journal of Molecular Biology, 1987, vol. 194, pp. 11-22.*
Murata et al. Simultaneous compairson of three protein structures. PNAS, 1985, vol. 82, pp. 3073-3077.*
Fenniri, "Method for Determining the Structure of an Active Member of a Chemical Library," United States Patent Application Publication, US 2002/0045266 A1, Apr. 18, 2002, U.S. Appl. No. 09/778,374.
Hogarth et al., "Three Dimensional Structures and Models of FC Receptors and Uses Thereof," United States Patent Application Publication, US 2002/0107359 A1, Aug. 8, 2002, U.S. Appl. No. 09/245,764.
Pitman et al., "Field-Based Similarity Search System and Method," United States Patent Application Publication, US 2003/0009298 A1, Jan. 9, 2003, U.S. Appl. No. 10/102,902.

(Continued)

*Primary Examiner*—Marjorie Moran
*Assistant Examiner*—Russell S Negin
(74) *Attorney, Agent, or Firm*—Daniel E. Johnson

(57) ABSTRACT

The virtual screening of a database of molecules is based on explicit three-dimensional molecular superpositions. The torsional flexibility of the database molecules is taken fully into account, and an arbitrary number of conformation-dependent molecular features may be considered. A fragmentation-reassembly approach is utilized, which allows for an efficient sampling of the conformational space. A fast clique-based pattern-matching algorithm generates alignments of pairs of adjacent molecular fragments on the (rigid) query molecule that are subsequently reassembled to complete database molecules. Using conventional molecular features (hydrogen bond donors and acceptors, charges, and hydrophobic groups), it is possible to rapidly produce accurate alignments of medium-sized drug-like molecules. Examples with a test database containing a diverse set of 1780 drug-like molecules (including all conformers) show that average query processing times of the order of 0.1 seconds per molecule can be achieved on a PC, depending on the size of the query molecule.

38 Claims, 26 Drawing Sheets

OTHER PUBLICATIONS

Rigoutsos et al., "Flexible 3D-Substructure Matching & Novel Conformer Derivation in Very Large Databases of 3D-Molecular Information," IBM Research Report, Jul. 10, 1996, 33 pgs.

Rigoutsos et al., "A New Method With Application to the Flexible Searching of 3D Molecular Databases," 19th Workshop Proceedings, Speedup Journal, vol. 10, No. 1-2, Switzerland, 1996, pp. 38-43.

Pitman et al., "Flashflood: A 3D Field-based similarity search and alignment method for flexible molecules," Journal of Computer-Aided Molecular Design, vol. 15, Jul. 2001, pp. 587-612.

G. Klebe et al., "Different approaches toward an automatic structural alignment of drug molecules: Applications to sterol mimics, thrombin and thermolysin inhibitors", Journal of Computer-Aided Mol. Design., vol. 8, 1994, pp. 751-778.

A. Kramer et al., "Fast 3D molecular superposition and similarity search in databases of flexible molecules", Journal of Computer-Aided Mol. Design., vol. 17, 2003, pp. 13-38.

S. Kearsley et al., "Flexibases: A way to enhance the use of molecular docking methods", Journal of Computer-Aided Mol. Design., vol. 8, 1994, pp. 565-582.

G. Klebe et al., "Methodological developments and strategies for a fast flexible superposition of drug-size molecules", Journal of Computer-Aided Mol. Design., vol. 13, 1999, pp. 35-49.

C. Lemmen et al., "Time-efficient flexible superposition of medium-sized molecules", Journal of Computer-Aided Mol. Design., vol. 11, 1997, pp. 357-368.

C. Lemmen et al., "RigFit: A new approach to superimposing ligand molecules", Journal of Computer-Aided Mol. Design., vol. 12, 1998, pp. 491-502.

J.E.J. Mills et al., "Slate: A Method for the superposition of flexible ligands", Journal of Computer-Aided Mol. Design., vol. 15, 2001, pp. 81-96.

D. A. Cosgrove, "A novel method of aligning molecules by local surface shape similarity", Journal of Computer-Aided Mol. Design., vol. 14, 2000, pp. 573-591.

C. McMartin et al., "Flexible matching of test ligands to a 3D pharmacophore using a molecular superposition force field: Comparison of predicted and experimental conformations of inhibitors of three enzymes", Journal of Computer-Aided Mol. Design, vol. 9, 1995, pp. 237-250.

R. Brown et al., "Use of Structure-Activity Data To Compare Structure-Based Clustering Methods and Descriptors for Use in Compound Selection", J. Chem. Inf. Comput. Sci., vol. 36, 1996, pp. 572-584.

P. Labute et al., "Flexible Alignment of Small Molecules", J. Med. Chem., vol. 44, 2001, 1483-1490.

Gordon C.K. Roberts, "Applications of NMR in drug discovery", DDT, vol. 5, No. 6, Jun. 2000, pp. 230-240.

A. Bondi, "van der Waals Volumes and Radii", The Journal of Physical Chem., vol. 68, No. 3, Mar. 16, 1964, pp. 441-451.

M. Clark et al., "Validatiion of the General Purpose Tripos 5.2 Force Field", Journal of Comp. Chem, vol. 10, No. 8, 1989, pp. 982-1012.

G. Crippen, "Quantitative Structure-Activity Relationships by Distance Geometry: Systematic Analysis of Dihydrofolate Reductase Inhibitors", J. of Med. Chem., vol. 23, No. 6, 1980, pp. 599-606.

J. Mason et al., "New 4-Point Pharmacophore Meth, for the mol. Similarity and Diversity Appl.: Overview of the Meth. and Appl., Incl. Novel Approach to the Design of Combinatorial Libraries Containing Privileged Substructures", J. Med. Chem, vol. 42, 1999, pp. 3251-3264.

J. Eksterowicz et al., "Coupling structure-based design with combinatorial chemistry: application of active site derived pharmacophores with informative library design", Journal of Mol. Graphics and Modeling. vol. 20, 2002, pp. 469-477.

R. Carbo et al., "How Similar is a Molecule to Another? An Electron Density Measure of Similarity between Two Molecular Structures", Intl. Journal of Quantum Chem., vol. XVII, 1980, pp. 1185-1189.

C. Humblet et al., "Chapter 29. 3D Database Searching and Docking Strategies", Annual Reports in Med. Chem. vol. 28, 1993, pp. 275-284.

Peter Willett, "Searching for Pharmacophoric Patterns in Databases of Three-dimensional Chemical Structures", Journal of Molecular Recognition, vol. 8, 1995, pp. 290-303.

C. Lemmen, "FLEXS: A Method for Fast Flexible Ligand Superposition", Journal of Med. Chem., vol. 41, 1998, pp. 4502-4519.

J. Grant et al., "A Fast Method of Molecular Shape Comparison: A Simple Application of a Gaussian Description of Molecular Shape", Journal of Comp. Chem. vol. 17, No. 14, 1996, pp. 1653-1666.

S. Handschuh et al., "Superposition of Three-Dimensional Chemical Structures Allowing for Conformational Flexibility by a Hybrid Method", J. Chem. Inf. Comput. Sci., vol. 38, No. 2, 1998, pp. 220-232.

C. Lemmen et al., "Computational methods for the structural alignment of molecules", J. of Computer-Aided Mol. Design., vol. 14, 2000, pp. 215-232.

C. Lemmen et al., "Multiple molecular superpositioning as an effective tool for virtual database screening", Perspectives in Drug Disc. and Design, vol. 20, 2000, pp. 43-62.

S. Kearsley et al., "An Algorithm for the Simultaneous Superposition of a Structural Series", Journal of Comp. Chem., vol. 11, No. 10, 1990, pp. 1187-1192.

R. Diamond et al., "On the multiple simultaneous superposition of molecular structures by rigid body transformations", Protein Science, vol. 1, 1992, pp. 1279-1287.

J. Mestres et al., "A molecular field-based similarity approach to pharmacophoric pattern recognition", Journal of Mol. Graphics and Mod., vol. 15, 1997, pp. 114-121.

M. Miller, "SQ: A Program for Rapidly Producing Pharmacophiorically Relevent Molecular Superpositions", Journal of Med. Chem., vol. 42, pp. 1505-1514, 1999.

\* cited by examiner

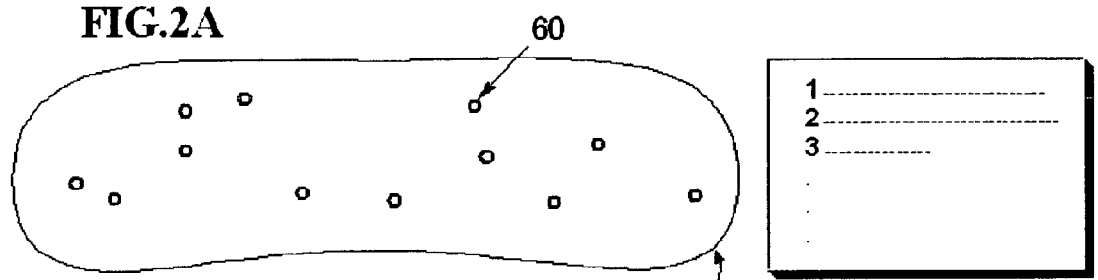
FIG. 2A
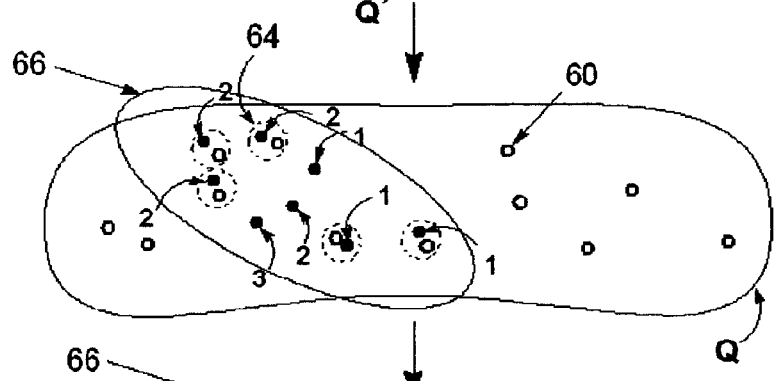
FIG. 2B
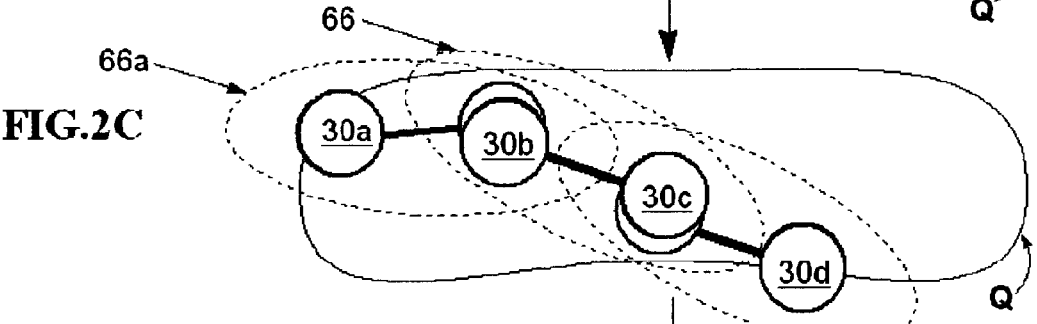
FIG. 2C
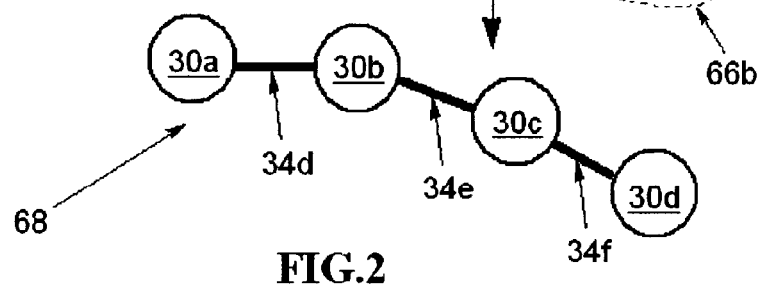
FIG. 2D
FIG. 2

| | |
|---|---|
| non-rotatable bonds | contained in ring structure,<br>leads to endpoint in the molecular graph (e.g. -H, or =O),<br>connects to methyl group $CH_3$,<br>connects to $CX_3$ (X=F,Cl) group,<br>connects to $NH_2$, where N is planar (N.pl3),<br>connects to C.2 in carboxyl group,<br>amide bonds between C.2 and N.am,<br>connects to O or S in -OH or -SH,<br>connects to $XO_3^-$ group (X=S.3,P.3; with 3 O.co2 attached) |
| "cis/trans" bonds<br>($0°$ and $180°$ rotations allowed) | bonds between C.2-C.2, C.ar-C.2, C.ar-N.x, C.ar-C.cat, C.2-C.cat, N.pl3-C.cat |
| rotatable bonds | all other bonds |

FIG.4

| feature type | feature location $x$ | vector geometry $p$ | Atom type | lookup index |
|---|---|---|---|---|
| *hydrogen bond donor* | | | | |
| OH or SH | atom | 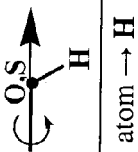 | O.3, S.3 (attached to one H) | 1 |
| other | atom | atom → H | N.3, N.2, N.ar<3>, N.am, N.pl3, N.4 with H attached | 1 |
| *hydrogen bond acceptor* | | | | |
| single tetrahedral | atom | 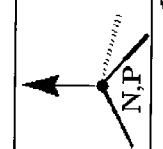 | N.3, P.3 | 2 |
| double tetrahedral | atom |  | O.3, S.3 (not attached to H) | 2 |
| single planar | atom |  | N.2, N.ar<2> | 2 |
| double planar | atom |  | O.2, S.2 | 2 |
| sulphone or phosphone (double) | atom | 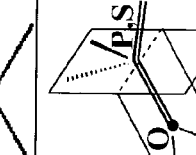 | O.2 | 2 |
FIG.6A

| feature type | feature location $x$ | vector geometry $p$ | Atom type | lookup index |
|---|---|---|---|---|
| hydrogen bond acceptor | | | | |
| single linear | atom | | N.1<1> | |
| -OH or -SH | atom | | O.3, S.3 (attached to one H) | 2 |
| carboxyl | | | C.2 (attached to two O.co2) | |
| amine oxide | atom | | O.3 (attached to N.4) | |
| base | | | | |
| | atom | | C.cat, N.ar<3>, N.4 | 3 |
| acid | | | | |
| carboxyl | | | C.2 (attached to two O.co2) | 4 |
| PO₃⁻ | atom | - | P.3 (attached to two O.co2) | |
| SO₃⁻ | atom | - | S.3 (attached to two O.co2) | |
| amine oxide | atom | - | O.3 (attached to N.4) | |
| hydrophobic | | | | |
| generic hydrophobic (see text) | atom ring center | - | C.3, C.2, C.1 (not neighbor of O,N,S,P) 6-ring with all C.ar | 5 |
| hydrophobic-aromatic | ring center | ring normal | 6-ring with all C.ar | 6 |

FIG.6B

| query molecule | database molecule | fragment pairs | conf's expanded | conf's processed | vote score | Carbo score | RMSD (RMSD$_{min}$) [Å] | CPU time [s] | vote score (rigid) | vote(flexible) / vote(rigid) |
|---|---|---|---|---|---|---|---|---|---|---|
| Thrombin inhibitors | | | | | | | | | | |
| 1dwc | 1dwc | 2 | 3.4*10$^6$ | 246 | 0.88 | 0.92 | 1.32 (1.28) | 2.7 | 1.0 | 0.88 |
| 1dwd | | | | | 0.68 | 0.80 | 2.42 (2.28) | 2.2 | 0.41 | 1.66 |
| 1dwc | 1dwd | 3 | 3.4*10$^6$ | 86 | 0.59 | 0.83 | 1.93 (1.93) | 0.5 | 0.41 | 1.44 |
| 1dwd | | | | | 0.91 | 0.83 | 2.26 (1.86) | 0.6 | 1.0 | 0.91 |
| H. rhinovirus coating protein | | | | | | | | | | |
| 2r04 | 2r04 | 2 | 2.0*10$^7$ | 333 | 1.0 | 0.95 | 1.37 (1.37) | 1.5 | 1.0 | 1.0 |
| 2r06 | | | | | 1.0 | 0.94 | 2.56 (1.49) | 1.5 | 0.66 | 1.52 |
| 2rr1 | | | | | 0.95 | 0.90 | R | 1.1 | 0.70 R | 1.36 |
| 2rs3 | | | | | 0.95 | 0.88 | R | 1.3 | 0.70 R | 1.36 |
| 2r04 | 2r06 | 2 | 5.5*10$^5$ | 179 | 1.0 | 0.91 | 1.90 (1.80) | 0.3 | 0.66 | 1.52 |
| 2r06 | | | | | 1.0 | 0.91 | 1.96 (1.28) | 0.4 | 1.0 | 1.0 |
| 2rr1 | | | | | 0.95 | 0.89 | R | 0.3 | 0.63 R | 1.51 |
| 2rs3 | | | | | 0.95 | 0.88 | R | 0.3 | 0.63 R | 1.51 |
| 2r04 | 2rr1 | 2 | 2.0*10$^7$ | 334 | 0.95 | 0.94 | R | 1.6 | 0.70 | 1.36 |
| 2r06 | | | | | 0.95 | 0.91 | R | 2.1 | 0.63 | 1.51 |
| 2rr1 | | | | | 1.0 | 0.92 | 1.64 (1.21) | 1.5 | 1.0 | 1.0 |
| 2rs3 | | | | | 1.0 | 0.91 | 1.29 (1.29) | 1.3 | 1.0 | 1.0 |
| 2r04 | 2rs3 | 2 | 1.2*10$^8$ | 749 | 0.95 | 0.90 | R | 2.2 | 0.70 R | 1.36 |
| 2r06 | | | | | 0.95 | 0.93 | R | 2.3 | 0.63 R | 1.51 |
| 2rr1 | | | | | 1.0 | 0.93 | 2.16 (1.66) | 1.8 | 1.0 | 1.0 |
| 2rs3 | | | | | 1.0 | 0.93 | 1.92 (1.64) | 1.7 | 1.0 | 1.0 |
| Fructose biphosphatase ligands | | | | | | | | | | |
| 4fbp | 4fbp | 2 | 216 | 9 | 0.89 | 0.99 | 0.52 (0.52) | 0.2 | 1.0 | 0.89 |
| t0039 | | | | | 0.63 | 0.96 | 0.57 (0.57) | 0.2 | 0.73 | 0.86 |
| 4fbp | t0039 | 2 | 432 | 6 | 0.74 | 0.95 | 0.61 (0.61) | 0.1 | 0.73 | 1.01 |
| t0039 | | | | | 0.90 | 0.98 | 0.61 (0.61) | 0.1 | 1.0 | 0.90 |

FIG. 10A

| query molecule | database molecule | fragment pairs | conf's expanded | conf's processed | vote score | Carbo score | RMSD (RMSD$_{min}$) [Å] | CPU time [s] | vote score (rigid) | vote(flexible) / vote(rigid) |
|---|---|---|---|---|---|---|---|---|---|---|
| \multicolumn{11}{l}{Dihydrofolate reductase inhibitors} |
| 1dhf | 1dhf | 2 | 31104 | 27 | 0.89 | 0.89 | 1.62 (1.54) | 0.1 | 1.0 | 0.89 |
| 4dfr |      |   |       |    | 0.70 | 0.87 | 1.73 (1.73) | 0.1 | 0.68 | 1.03 |
| 1dhf | 4dfr | 2 | 31104 | 32 | 0.70 | 0.91 | 2.69 (2.30) | 0.2 | 0.68 | 1.03 |
| 4dfr |      |   |       |    | 0.86 | 0.86 | 1.84 (1.84) | 0.2 | 1.0 | 0.86 |
| \multicolumn{11}{l}{Thermolysin inhibitors} |
| 1tlp | 1tlp | 2 | 6.0*10$^7$ | 722 | 0.76 | 0.94 | 1.76 (1.48) | 92.0 | 1.0 | 0.76 |
| 1tmn |      |   |       |    | 0.54 | 0.86 | 3.11 (2.94) | 9.4 | 0.57 | 0.95 |
| 2tmn |      |   |       |    | X    | X    | X           | 1.1 | 0.37 | X |
| 3tmn |      |   |       |    | 0.51 | 0.68 | 3.86 (3.86) | 5.3 | 0.63 | 0.81 |
| 1tlp | 1tmn | 2 | 3.6*10$^8$ | 1305 | 0.52 | 0.70 | 3.54 (3.43) | 11.8 | 0.57 | 0.91 |
| 1tmn |      |   |       |    | 0.92 | 0.89 | 2.20 (1.85) | 20.7 | 1.0 | 0.92 |
| 2tmn |      |   |       |    | X    | X    | X           | 0.8 | 0.42 | X |
| 3tmn |      |   |       |    | 0.72 | 0.75 | 4.10 (3.70) | 3.8 | 0.85 | 0.85 |
| 1tlp | 2tmn | 1 | 1296 | 25 | 0.37 | 0.65 | 1.88 (1.10) | 0.1 | 0.37 | 1.0 |
| 1tmn |      |   |       |    | 0.42 | 0.69 | 2.00 (1.24) | 0.1 | 0.42 | 1.0 |
| 2tmn |      |   |       |    | 1.0  | 0.96 | 1.42 (0.97) | 0.1 | 1.0  | 1.0 |
| 3tmn |      |   |       |    | 0.46 | 0.72 | 1.34 (1.22) | 0.1 | 0.46 | 1.0 |
| 1tlp | 3tmn | 2 | 46656 | 20 | 0.58 | 0.76 | 1.36 (1.25) | 0.1 | 0.63 | 0.92 |
| 1tmn |      |   |       |    | 0.85 | 0.82 | 1.24 (1.24) | 0.1 | 0.85 | 1.0 |
| 2tmn |      |   |       |    | X    | X    | X           | 0.1 | 0.46 | X |
| 3tmn |      |   |       |    | 1.0  | 0.90 | 1.25 (1.00) | 0.1 | 1.0  | 1.0 |
| \multicolumn{11}{l}{Carboxypeptidase A inhibitors} |
| 1cbx | 1cbx | 1 | 216 | 12 | 1.0  | 0.96 | 0.88 (0.88) | 0.1 | 1.0  | 1.0 |
| 6cpa |      |   |     |    | 0.46 | 0.61 | 1.03 (1.03) | 0.1 | 0.46 | 1.0 |
| 7cpa |      |   |     |    | 0.44 | 0.53 | 1.13 (1.13) | 0.1 | 0.44 | 1.0 |
| 1cbx | 6cpa | 2 | 3.6*10$^8$ | 384 | X | X | X | 0.3 | 0.46 | X |

FIG. 10B

| query molecule | database molecule | fragment pairs | conf's expanded | conf's processed | vote score | Carbo score | RMSD (RMSD$_{min}$) [Å] | CPU time [s] | vote score (rigid) | vote(flexible) / vote(rigid) |
|---|---|---|---|---|---|---|---|---|---|---|
| \multicolumn{11}{c}{Carboxypeptidase A inhibitors} ||||||||||
| 6cpa | 6cpa | 2 | 3.6*10$^8$ | 384 | 0.79 | 0.88 | 1.61 (1.37) | 11.6 | 1.0 | 0.79 |
| 7cpa | | | | | 0.67 | 0.81 | 1.60 (1.39) | 10.6 | 0.87 | 0.77 |
| 1cbx | 7cpa | 3 | 1.3*10$^{15}$ | 1187 | X | X | X | 0.8 | 0.44 | X |
| 6cpa | | | | | X | X | X | 24.3 | 0.87 | X |
| 7cpa | | | | | 0.77 | 0.87 | 2.40 (2.32) | 46.6 | 1.0 | 0.77 |
| \multicolumn{11}{c}{Elastase inhibitors} ||||||||||
| 1ela | 1ela | 2 | 2.0*10$^7$ | 262 | 1.0 | 0.95 | 1.46 (0.89) | 3.0 | 1.0 | 1.0 |
| 1ele | | | | | 0.83 | 0.92 | 1.98 (1.08) | 2.2 | 0.87 | 0.95 |
| 1ela | 1ele | 2 | 15552 | 121 | 0.72 | 0.83 | 1.24 (1.22) | 0.5 | 0.87 | 0.83 |
| 1ele | | | | | 0.84 | 0.77 | 2.15 (1.20) | 0.5 | 1.0 | 0.84 |

FIG.10C

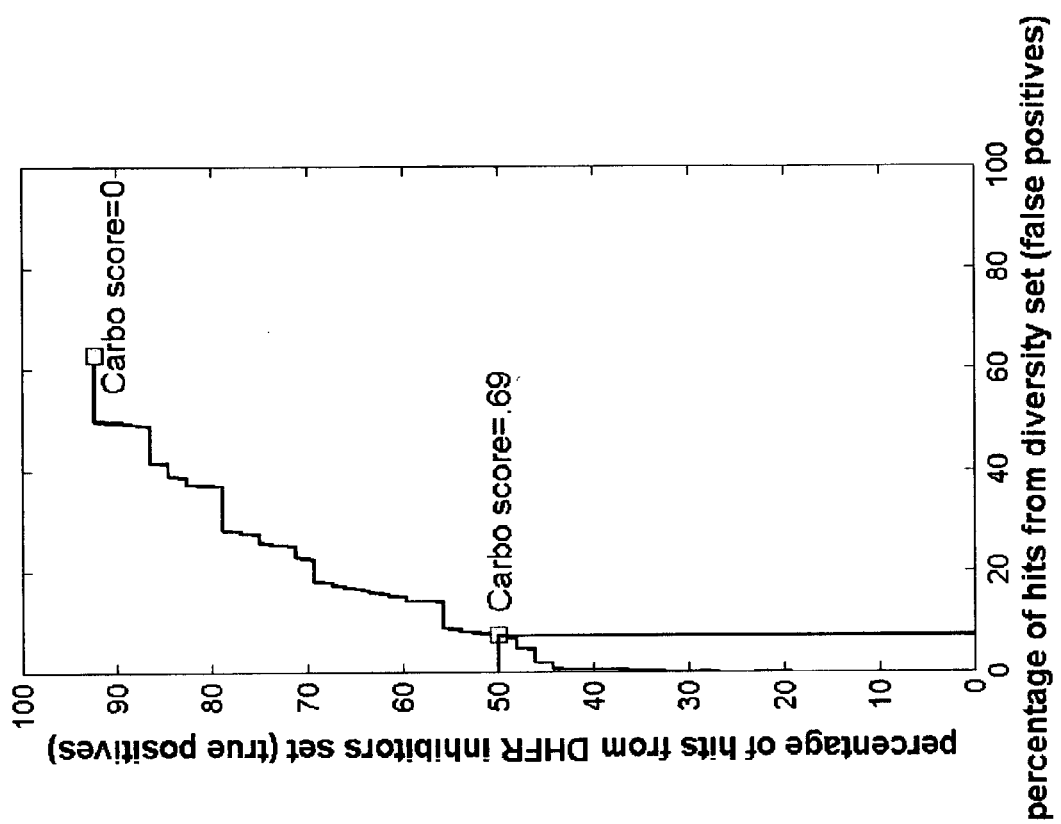
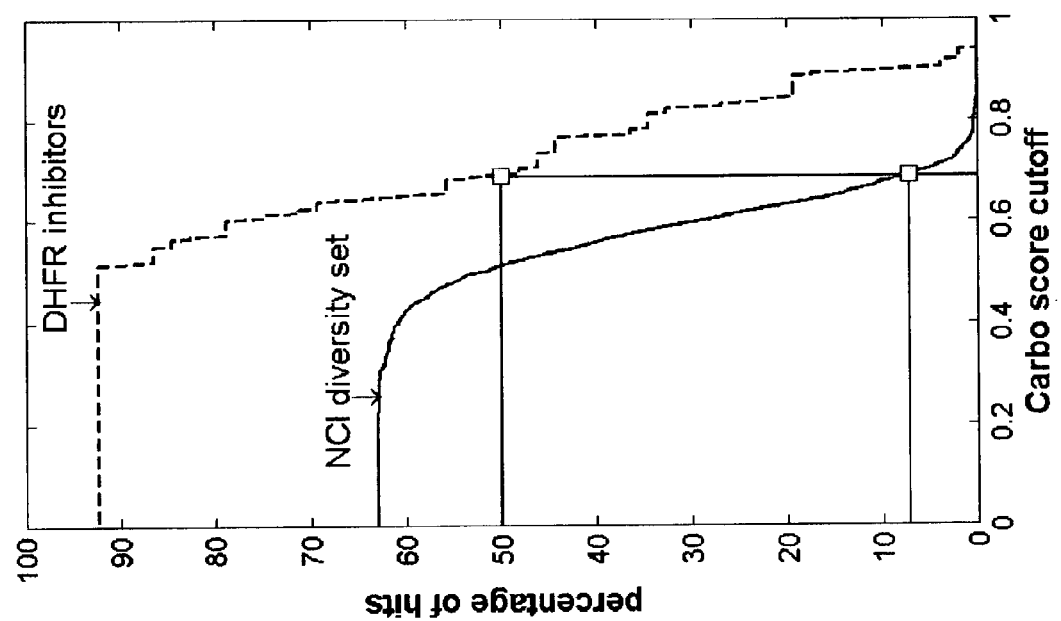
FIG.15C
FIG.15B

| query molecule | number of | | CPU time [s] |
|---|---|---|---|
| | atoms | features | |
| 1dhf | 51 | 19 | 0.095 |
| 4dfr | 54 | 19 | 0.080 |
| 1dwc | 71 | 20 | 0.11 |
| 1ela | 64 | 17 | 0.067 |
| 1tlp | 69 | 27 | 0.45 |
| 1tmn | 67 | 18 | 0.070 |
| 2r04 | 51 | 11 | 0.036 |
| 4fbp | 35 | 15 | 0.10 |
| 6cpa | 58 | 22 | 0.22 |
| 7cpa | 74 | 23 | 0.30 |

FIG.16

METHOD OF PERFORMING THREE-DIMENSIONAL MOLECULAR SUPERPOSITION AND SIMILARITY SEARCHES IN DATABASES OF FLEXIBLE MOLECULES

TECHNICAL FIELD

The invention relates to a method of searching a database to identify at least one compound that has both a conformation and a physico-chemical property similar to those of a query molecule.

BACKGROUND

The virtual screening of compounds in databases is an important tool in modern drug design. Traditionally, two-dimensional or pharmacophore-based methods, which are very fast but have only limited accuracy, have been used for this purpose. (See, for example, H. Matter et al., in Combinatorial Organic Chemistry, John Wiley & Sons, New York, N.Y., 1999; C. Humblet et al., Annual Reports in Medicinal Chemistry, vol. 28, Chapter VI, Topics in Drug Design and Discovery, Academic Press, London, pp. 275-284, 1993; P. Willet, J. Mol. Recognition, vol. 8, p. 290, 1995; and R. D. Brown et al., J. Chem. Inf. Comput. Sci., vol. 36, p. 572, 1996.)

Three-dimensional molecular superposition methods have been successfully utilized to determine binding geometries relative to a reference molecule. (See, for example, G. Klebe et al., J. Comput. Aided Mol. Des., vol. 8, p. 751, 1994; S. K. Kearsley, et al., J. Comput. Aided Mol. Des., vol. 8, p. 565, 1994; G. Klebe et al., J. Comput. Aided Mol. Des., vol. 13, p. 35, 1999; C. Lemmen et al., J. Comput. Aided Mol. Des., vol. 11, p. 357, 1997; C. Lemmen, J. Med. Chem., vol. 41, p. 4502, 1998; C. Lemmen et al., J. Comput. Aided Mol. Des., vol. 12, p. 491, 1998; M. D. Miller et al., J. Med. Chem., vol. 42, p. 1505, 1999; J. A. Grant et al., J. Comput. Chem., vol. 17, p. 1653, 1996; C. McMartin et al., J. Comput. Aided Mol. Des., vol. 9, p. 237; and S. Handschuh et al., J. Chem. Inf. Comput. Sci., vol. 38, p. 220, 1998.) These 3-D methods play an important role in 3D-QSAR (Quantitative Structure-Activity Relationships) applications, pharmacophore elucidation, and receptor modeling—situations in which structural data of the target protein is not available. The variety of methodologies used for molecular superposition has recently been extensively reviewed (see Lemmen et al., J. Comput. Aided Mol. Des., vol. 14, p. 215, 2000), and an application of existing superposition methods to virtual database screening has been reported (see C. Lemmen et al., Perspectives in Drug Discovery and Design, vol. 20, p. 43, 2000).

Of course, the use of molecular superposition to determine the binding capability of possible ligands has its limitations. The underlying assumption is that other ligands will have the same overall binding mode as the reference molecule. Also, the bound conformation of the reference molecule has to be known, which is generally true only if crystallographic information about the corresponding protein-ligand complex is available. Therefore, in practical applications, the reference molecule should have a non-flexible structure, or its bound conformation has to be inferred using other methods, e.g., deduced from simultaneous, flexible alignments within a set of ligands that are known to be active. (See, for example, S. K. Kearsley et al., J. Comput. Chem., vol. 11, p. 1187, 1990; R. Diamond, Protein Sci., vol. 1, p. 1279, 1992; J. Mestres et al., J. Mol. Graph., vol. 15, p. 114, 1997; D. A. Cosgrove et al., J. Comput. Aided Mol. Des., vol. 14, p. 573, 2000; P. Labute et al., J. Med. Chem., vol. 44 p. 1483, 2001; and J. E. J. Mills et al., J. Comput. Aided Mol. Des., vol. 15, p. 81, 2001.) The bound conformation of the reference molecule can also be determined from distance constraints obtained in NMR (NOE) experiments (see G. C. K. Roberts, Drug Discovery Today, vol. 5, p. 230, 2000).

A field-based similarity search system and method have been described in which there is no screening of the conformation space, leading to a high computational load (see M. C. Pitman et al., J. Comput. Aided Mol. Des., vol. 15, p. 587, 2001). In this approach, all candidate molecules must first be assembled before they are scored. U.S. Pat. Nos. 5,787,279 and 5,752,019 to Rigoutsos describe other search systems and methods in which the search is based on atom types, and pose-clustering (a particular method of clustering of coordinate systems arbitrarily located and rotated in space) is used to generate alignments (hypotheses).

There is still a need for an accurate, efficient method of performing a database search of molecules that fully accounts for the three-dimensional structure and conformational flexibility of the molecules in the database.

SUMMARY

Highly efficient methods are described herein for searching a database for molecules having a conformation and at least one physico-chemical property similar to those of a reference or query molecule. The methods herein have been used to screen a database of about 1800 molecules within a few minutes on a low-end PC, while producing accurate 3D molecular alignments. Preferred methods rely on conformational flexibility and clique search type algorithms to generate explicit three-dimensional superpositions. These methods are faster than other methods of comparable accuracy used to produce conformations suitable for molecular superpositions. The methods herein are both fast and accurate, as opposed to field based approaches that tend to be slow and do not deliver the desired accuracy. One advantage of preferred methods herein is that a course graining approach is used to remove redundant conformations from the conformational space, thereby avoiding unnecessary computational load. Another advantage of preferred methods herein is that candidate molecules (or fragments) need not be assembled before they are scored, but can be first scored on a directed graph basis without expensive computation. The fragmentation-reassembly procedure disclosed herein is used to significantly speed up query processing.

Yet another advantage of preferred methods herein is that molecules are represented using point-like features, including features known to be important in protein-ligand binding, e.g., hydrogen bond donors, acceptors, charges and hydrophobic regions. Furthermore, more sophisticated feature schemes may be used, such as using certain molecular surface properties, since features may explicitly depend on the molecular conformation. Using point-like features is by its nature different from using field-based features, leading to substantially improved performance.

In order to enable fast query processing during database searches, as much computational work as possible is preferably done in a database pre-processing step in which physico-chemical features are calculated from molecular properties. During preprocessing, millions of conformations may be explored by uniform sampling of dihedral angles, with many of them being discarded because of internal steric clashes or because the generated conformational change is too small relative to a conformation already stored in the database.

In preferred methods herein, the virtual screening of a database of molecules is based on explicit three-dimensional molecular superpositions that take the torsional flexibility of the database molecules fully into account. Molecules are represented by an arbitrary number of point-like features that are allowed to explicitly depend on the conformation of molecular fragments. An extensive database pre-processing step is used during which features are pre-calculated and stored in a lookup table in order to minimize computer time needed for a database query. Using a conventional molecular feature definition (hydrogen bond donors and acceptors, charges, and hydrophobic groups), the methods are able to rapidly produce accurate alignments for a test set of pairs of medium-sized drug-like molecules, which are known to bind to the same receptor. Using a test database containing a diverse set of 1728 drug-like molecules from the National Cancer Institute (NCI) diversity set as well as 52 dihydrofolate reductase actives, it has been demonstrated that average query processing times of the order of 0.1 seconds per molecule (including all conformers) can be achieved on a PC. The preferred algorithm is naturally parallelizable (i.e., all database molecules are processed independently of each other), suggesting that methods herein can be scaled to run on a farm of 50 or more PCs, permitting a database of several hundred thousand molecules to be searched in a few minutes.

One aspect of the invention is a method of identifying at least a portion of a molecule indexed in a database, with the database preferably being populated as part of a pre-processing procedure. The molecule has both a conformation and at least one physico-chemical property similar to those of a query molecule provided by a user of the method. The database includes at least one conformation representation of each of the indexed molecules, in which each of the indexed molecules is partitioned into a set of overlapping fragments, and in which at least one conformation representation is associated with each fragment. For each of the fragment conformation representations, at least 3 features of interest of the fragment are provided, and each of said at least 3 features represent at least one given physico-chemical property and is associated with a respective point in 3-D space. The method includes providing a conformation of a query molecule that includes at least 3 features, each of which corresponds to at least one physico-chemical property of interest and is associated with a respective point in 3-D space. The method further includes pattern matching features of the query molecule with corresponding features of fragments given by fragment conformation representations in the database to identify fragments having patterns of features similar to patterns of features in portions of the query molecule, in which the pattern matching includes i) first matching just feature type and ii) the matching feature geometry. The method also includes assembling geometrically compatible overlapping fragment conformations corresponding to fragments identified by the pattern matching into at least one three-dimensional molecular structure that corresponds to at least a portion of at least one of the indexed molecules, in order to identify at least a portion of a molecule in the database having patterns of features similar to patterns of features in the query molecule.

In a preferred method, this three-dimensional molecular structure corresponds to at least one entire indexed molecule. The method may further comprise, for each one of the overlapping fragments, calculating a set of conformations by sampling torsional angles corresponding to rotatable bonds of said one of the overlapping fragments. The method may further comprise using a graph-based algorithm for at least one of the pattern matching and the assembling. In a preferred method, the fragment conformations include conformations corresponding to fragments that have at least 20 atoms. In addition, the overlapping fragments may be constructed from pairs of adjacent non-overlapping fragments separated by one rotatable bond. The assembling may be based on the detection of directed paths in a directed graph having vertices representing the adjacent non-overlapping fragments, and may include scoring of the three-dimensional molecular structures without using their three-dimensional coordinates. In a preferred method, the conformations corresponding to the associated conformation representations are selected by avoiding processing two or more overlapping fragment conformations during a database query if those overlapping fragment conformations are not sufficiently distinct from each other by a predetermined measure. In preferred methods, the pattern matching includes identifying feature pairs, in which each feature pair includes a feature in the query molecule and a corresponding feature in a database molecule. Also, the pattern matching is preferably based on clique-detection in a distance-compatibility graph and does not require knowledge of local coordinate systems. The features of the fragments may represent at least one of the following physico-chemical properties: hydrogen bond donors, hydrogen bond acceptors, hydrophobic regions, aromatic rings, acid groups, and base groups; at least some of the features of the query molecule may be located somewhere other than at atomic sites. The method may include calculating said at least 3 features of the query molecule, calculating the features of the fragments of the indexed molecules, and partitioning the indexed molecules by an automated procedure using an algorithm that minimizes the number of conformations to be stored in the database.

A preferred embodiment of the invention is a product comprising a computer-readable medium that tangibly embodies a computer executable program thereon. The program is designed for identifying at least a portion of a molecule indexed in a database, in which the molecule has both a conformation and at least one physico-chemical property similar to those of a query molecule provided by a user of the program. The database includes at least one conformation representation of each of the indexed molecules, in which each of the indexed molecules is partitioned into a set of overlapping fragments, and in which at least one conformation representation is associated with each fragment, and in which for each of the fragment conformation representations, at least 3 features of interest of the fragment have been provided, each of said at least 3 features representing at least one given physico-chemical property and being associated with a respective point in 3-D space. In response to a user of the program providing a conformation of the query molecule that includes at least 3 features, each of which corresponds to at least one physico-chemical property of interest and is associated with a respective point in 3-D space, the program has instructions for pattern matching features of the query molecule with corresponding features of fragments given by fragment conformation representations in the database to identify fragments having patterns of features similar to patterns of features in portions of the query molecule, in which the pattern matching includes i) first matching just feature type and ii) then matching feature geometry. The program further includes instructions for assembling geometrically compatible overlapping fragment conformations corresponding to fragments identified by the pattern matching into at least one three-dimensional molecular structure that corresponds to at least a portion of at least one of the indexed molecules, in order to identify at least a portion of a molecule in the database having patterns of features similar to patterns of features in the query molecule.

BRIEF DESCRIPTION OF THE DRAWINGS

FIG. 2, which includes FIGS. 2A, 2B, 2C, and 2D, schematically illustrates the steps involved in assembling a candidate molecule similar to a query molecule Q.

FIG. 4 presents definitions of rotatable and non-rotatable bonds using SYBYL® atom types.

FIG. 6, which includes FIGS. 6A and 6B, presents feature definitions based on SYBYL® atom types.

FIG. 10, which includes FIGS. 10A, 10B, and 10C, presents results of molecular superposition examples using the methods disclosed herein.

FIG. 12, which includes

FIG. 16 presents the average processing time per molecule for queries against the test database, in which a PC with a 1.8 GHz Pentium 4 processor was used.

DETAILED DESCRIPTION OF THE PREFERRED EMBODIMENTS

A preferred similarity search algorithm is described followed by a discussion of working examples designed to test the capabilities of preferred methods with regard to computational performance and the accuracy of molecular alignments. The working examples presented in section 2.2 are mutual alignments of medium-sized molecules taken from the FlexS™ benchmark test set (see C. Lemmen et al. on the Internet website identified by the concatenation of "http://" and "www.biosolveit.de", and C. Lemmen, J. Med. Chem., vol. 41, p. 4502, 1998.) In section 2.3, methods are presented in which molecules similar to a given query molecule are found within a large, diverse set of 1780 molecules. For this purpose, a database was prepared that contained a diverse set of 1728 compounds as well as a smaller set of 52 molecules that are active towards the same receptor as a selected query molecule, which was included in the smaller set.

1. Algorithm

The preferred algorithm for determining whether two molecules are similar entails representing a molecule by a set of features located at certain points in space. A feature of a molecule (or a portion of a molecule) is one or more properties associated with a single point in 3-dimensional space that may include directional or orientational information related to that property or properties. This point is not necessarily coincident with an atomic site, and may, for example, lie on the surface of the molecule. There are various rotationally invariant types of features corresponding to different local physico-chemical properties of the molecule. These can be atom-based entities like hydrogen bond donors and acceptors or charges, as well as local properties, which are not necessarily related to atoms or functional groups. For instance, a feature may describe local geometry or quantities that have been derived from a continuous field.

Specifically, a molecule D (or more generally, a portion of the molecule) is said to be similar to given conformation of a query molecule Q (which is treated as rigid) if a conformation of D exists that can be aligned with Q such that a certain number of features on Q and D match with respect to feature type and location within a certain tolerance. The number of matching features (subsequently referred to as "votes") is determined along with a Carbo score. (See, for example, R. Carbo et al., Int. J. Quant. Chem., vol. 17, p. 1185, 1980). The Carbo score characterizes the overall molecular overlap and is used to construct a final similarity score (see section 2.1) that measures the similarity between Q and D. The goal is to find those molecules D in a database that can be aligned to a given conformation of a query molecule Q such that the similarity score is larger than a given value.

Figures 1, 1A, 1B, 1C, 1D:
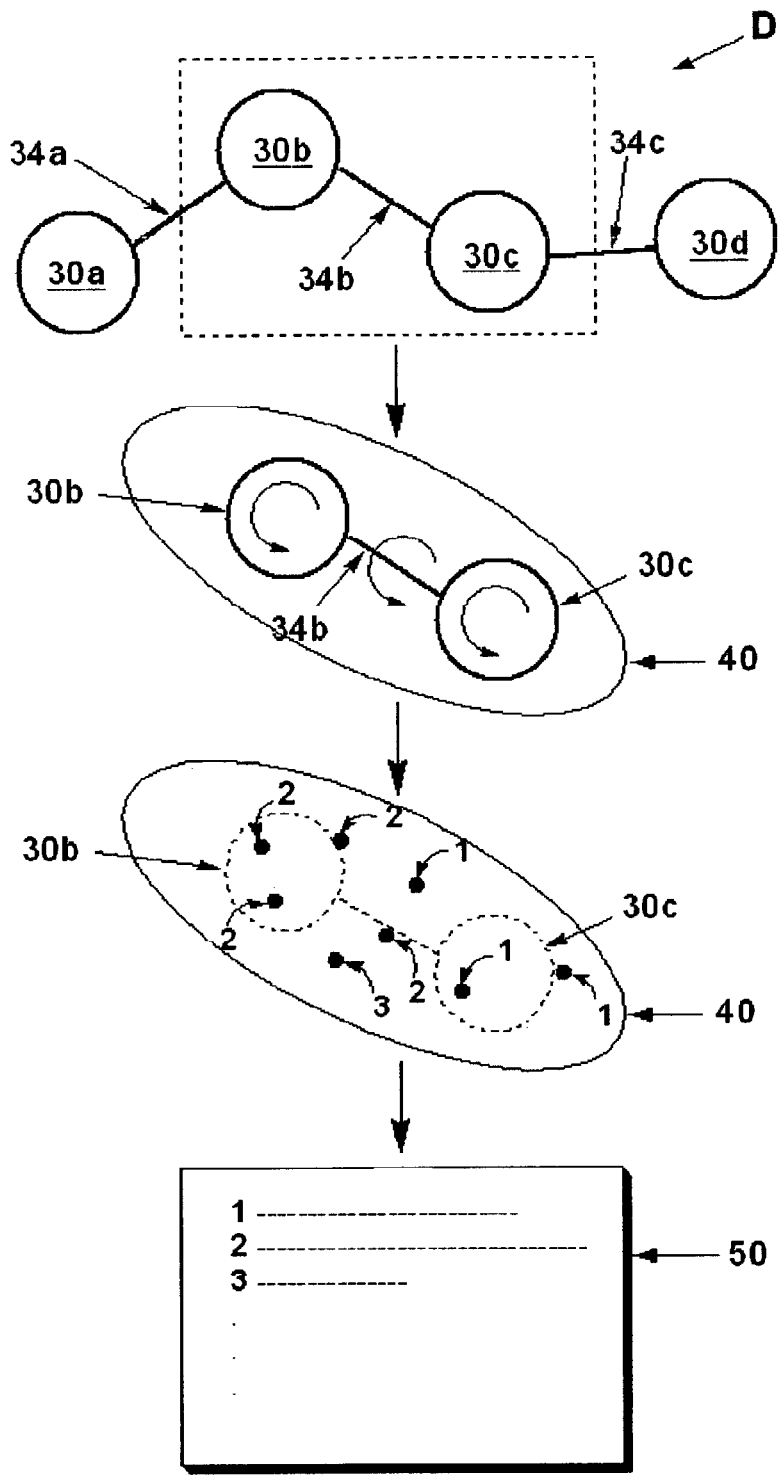
FIG. 1, which includes FIGS. 1A, 1B, 1C, and 1D, schematically illustrates a series of pre-processing steps leading to construction of a lookup table, in which the feature type serves as the lookup index.

A preferred similarity search procedure is illustrated in FIGS. 1 and 2. It includes a database pre-processing step (see FIG. 1), which only needs to be carried out once, as well as an actual database query (see FIG. 2). This search procedure is briefly outlined here and is described in greater detail below. During the preprocessing step, all the database molecules D are partitioned into disjoint fragments 30a, 30b, 30c, 30d (see FIG. 1A, which for clarity only shows four such fragments, which are typically groups of 10 or more atoms) that are connected by rotatable bonds 34a, 34b, 34c (see section 1.1 below). The fragments are each expanded into a set of conformations such that a) the conformational space is sampled up to a certain accuracy (measured by root mean square distance or "RMSD"; see section 2.2) and b) there are no steric clashes between non-bonded atoms. The coordinates of all fragment conformations are then explicitly stored in the database. For simplicity, the special case of "linear-chain" fragmentation is considered here, in which each fragment is connected to one or two other fragments. Next, adjacent fragments are joined into fragment pairs (so that each fragment pair typically includes 20 or more atoms) whose conformations are expanded with respect to the dihedral angle at the connecting bond (see FIG. 1B, which shows the fragment pair 40 that includes fragments 30b and 30c). However, it is preferable to formulate a representation of each fragment pair conformation by storing only the rules (i.e., the rotations and translations to be applied to the two fragments) needed to make a fragment pair, as opposed to storing the fragment pair coordinates explicitly. Features for the fragment pair conformation are then calculated (see section 1.3 and FIG. 1C, which shows three types of features 1, 2, 3 on the fragment pair 40). The use of overlapping fragment pairs instead of fragments in the feature computation reduces the influence of boundary effects. Information about each feature, including a reference to the corresponding fragment pair and its location in space, is stored in a central lookup table 50 using the feature type as the lookup index (see FIG. 1D, section 2.3, and FIG. 6). The feature type (e.g., hydrogen bond donor or acceptor) serves as the lookup index, and different feature types will in general have a different number of entries (see FIG. 6 and Section 1.4).

When querying the database, entries are retrieved from the lookup table 50 for each feature 60 associated with the given conformation of the query molecule Q (see FIG. 2A, FIG. 6, and section 1.4). Using clique detection (see, for example, G. Chartrand, Introductory Graph Theory, Dover, 1985), patterns of features (corresponding to the feature correspondences 64 in FIG. 2B) on fragment pairs stored in the look-up table 50 are geometrically matched with similar feature patterns on the query molecule Q, thereby producing an alignment 66 of the fragment pair onto the query molecule; such an alignment is referred to herein as a "hypothesis". As shown in FIG. 2C, the query procedure generates multiple hypotheses; hypotheses 66a and 66b are shown and have in common with hypothesis 66 the fragments 30b and 30c, respectively. As shown in FIGS. 2C and 2D, hypotheses are then assembled to form one or more whole molecules (referred to as "candidates") 68 using a graph-based algorithm, which is based on pair-wise compatibility of hypotheses (see section 1.5). Candidate 68 is a different conformation of the database molecule D and is aligned onto the query molecule Q, in which the rotatable bonds 34d, 34e, 34f of FIG. 2D connecting the fragments 30a, 30b, 30c, 30d are now different from the rotatable bonds 34a, 34b, 34c of FIG. 1A. All candidates are scored, and a final bump check is performed (see section 1.2).

The size of the molecular fragments is determined by a trade-off between the total number of conformations that must be processed during a database query and the selectivity of single pattern matches. Fragment pairs that are too large will generally exhibit too many internal conformations. On the other hand, fragment pairs that are too small will have only a few feature points and therefore produce many unspecific placements on the query molecule, so that a meaningful assembly of complete molecules is not possible. Molecules are typically divided into 1 to 3 fragment pairs, each of which contains between 20 and 40 atoms and about 10 feature points. The method does not require any special base fragment from which an incremental assembly procedure is started.

Various steps of the preferred similarity search algorithm are now described in greater detail.

1.1 Fragmentation

Figure 3:
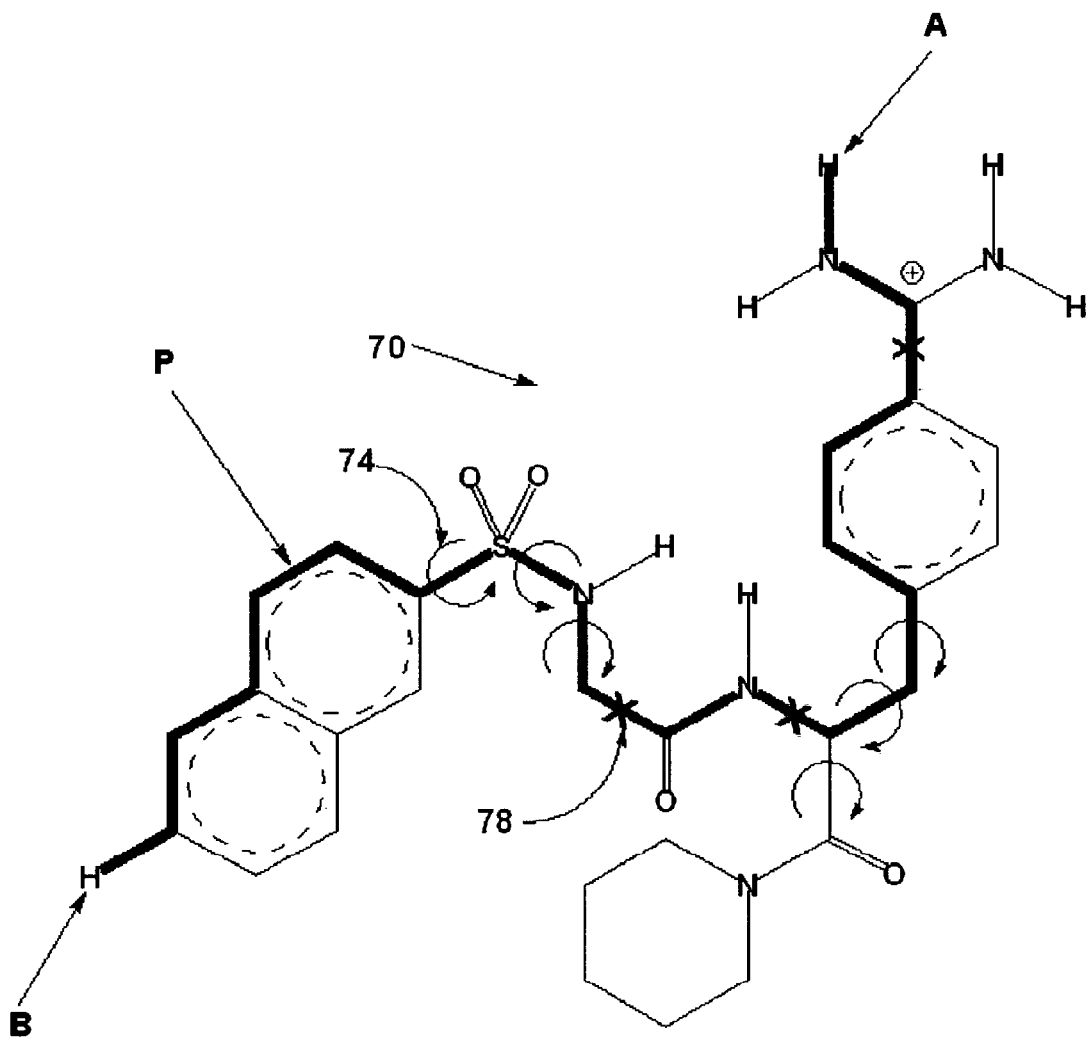
FIG. 3 is an illustration of the automatic molecular fragmentation procedure.

Fragmentation of a molecule is preferably an automated process that results in the identification of a set of rotatable bonds where the molecule is cut. This set of rotatable bonds is determined such that the total number of fragment pair conformations is minimized given the minimum fragment pair size and the sampling resolution $\Delta\phi$ of the dihedral angles. The algorithm used for automatic partitioning of a molecule is discussed with reference to the molecule 70 shown in FIG. 3. Briefly, the algorithm determines that path in the molecular graph containing the largest number of rotatable bonds 74. The molecule 70 can then in principle be cut at each rotatable bond 74 along this path. The number and actual location of the cuts 78 is chosen such that the number of fragment pair conformations is minimal given a certain fragment pair size.

First, all those bonds 74 that are rotatable are determined. A distinction is made between those bonds that are expected to be more or less freely rotatable (e.g., C—C single bonds between carbon atoms) and those expected to exist in two (cis/trans) conformations corresponding to $\Delta\phi=0°$ and $180°$ (e.g., C=C double bonds). The criteria used to determine whether a particular bond is a) considered to be rotatable or b) may exist in two different states ("cis/trans") are listed in FIG. 4, which defines rotatable and non-rotatable bonds using SYBYL® atom types (see M. Clark et al., J. Comput. Chem. 10, p. 982, 1989).

Bonds which connect to a terminal group that is nearly rotationally symmetric ($CH_3$, $CX_3$ (X=F, Cl), $SO_3^-$, $PO_3^-$) are considered here to be non-rotatable. Special cases include hydroxyl, SH, and carboxyl groups which are treated as being rigid, i.e., the dihedral angle is not expanded explicitly, but features (see section 1.3) on these groups are defined in a way that their inherent flexibility is taken into account. Ring conformations are also considered rigid.

The algorithm treats the molecule in question as a "graph" and determines a path P (denoted by the solid line in FIG. 3) through this "molecular graph" that contains those rotatable bonds at which the molecule may be cut into fragments. This is done by assigning a weight $\epsilon$ of 1 to each edge of the molecular graph, which represents a rotatable bond, and a small weight $\epsilon$ for each non-rotatable one. Dijkstra's algorithm (see, for example, R. Sedgewick, Algorithms in C++, Addison-Wesley, New York, 1992) is then used for finding shortest paths in a graph to determine the pair of atoms A and B for which the shortest path between A and B has the maximal length for all atom pairs in the molecule. Specifically, the "endpoints" of the molecule are first defined, with the endpoints being those atoms bonded to only one other atom. Next, the shortest path (as defined by the number of "atomic hops" from one atom to an adjacent atom needed to go from one endpoint to another endpoint) between every pair of these endpoints is calculated. Finally, the longest one of these paths is identified.

The parameter $\epsilon$ should be larger than 0 in order to ensure stability of the algorithm, so here $\epsilon$ is chosen to be 0.1. In the limit $\epsilon \rightarrow 0$, the length of the path P corresponds to the number of rotatable bonds along P. The procedure described above minimizes the number of rotatable bonds not contained in the path P, and therefore maximizes the number of "cuttable" bonds. This works well for molecules that have few branches. Finally, an exhaustive search of all possible fragmentations involving cuts at the rotatable bonds along P is performed to find the optimal set of rotatable bonds to be cut such that the total number of fragment pair conformations (to be stored in the database) is minimized given the minimum fragment pair size and the sampling resolution Δφ of the dihedral angles. The minimum fragment pair size is chosen to ensure meaningful extended pattern matches in the 3D pattern matching procedure (see section 1.4). A minimum fragment pair size of 25-30 atoms works well, resulting in fragment pairs built from fragments that typically contain more than one rotatable bond (as opposed to the methods disclosed in U.S. Pat. Nos. 5,787,279 and 5,752,019 to Rigoutsos, in which the fragments are constrained to be rigid, i.e., to not have rotatable bonds).

1.2 Sampling of Conformational Space

Molecular conformations are generated by uniformly sampling the dihedral angles of all rotatable bonds with a certain angular resolution Δφ. In the preprocessing step this is done for all fragments and all fragment pairs of the database molecules, and a bump check is performed that removes conformations for which the distance between any two non-bonded atoms is smaller than 0.65 times the sum of the respective atomic van der Waals radii (as taken from A. Bondi, J. Phys. Chem., vol. 68, p. 441, 1964). This avoids the possibility of near coincident atoms in the conformation.

Since the number of stored conformations should be as small as possible in order to minimize the query processing time, a subsequent "coarse graining" step is performed to ensure that the mutual RMSD (after minimization with respect to translations and rotations) of all pairs of conformations is larger than a certain threshold μ. This is done by scanning through all conformations generated by the angular expansion procedure and removing all those whose RMSD with respect to any previously encountered conformation is smaller than μ. Since the RMSD represents a metric in the space of conformations, this can be done efficiently by making use of the triangle inequality. The parameter μ should reflect the expected accuracy (in terms of the RMSD) of the final candidate alignments on the query molecule; a value of 1 Å has been found to work well. In order to ensure that all fragment pairs are built from the same set of fragment conformations, the coarse graining procedure is performed first on the fragment level and then again after sampling the dihedral angle of the connecting bond on a fragment pair.

Figure 5:
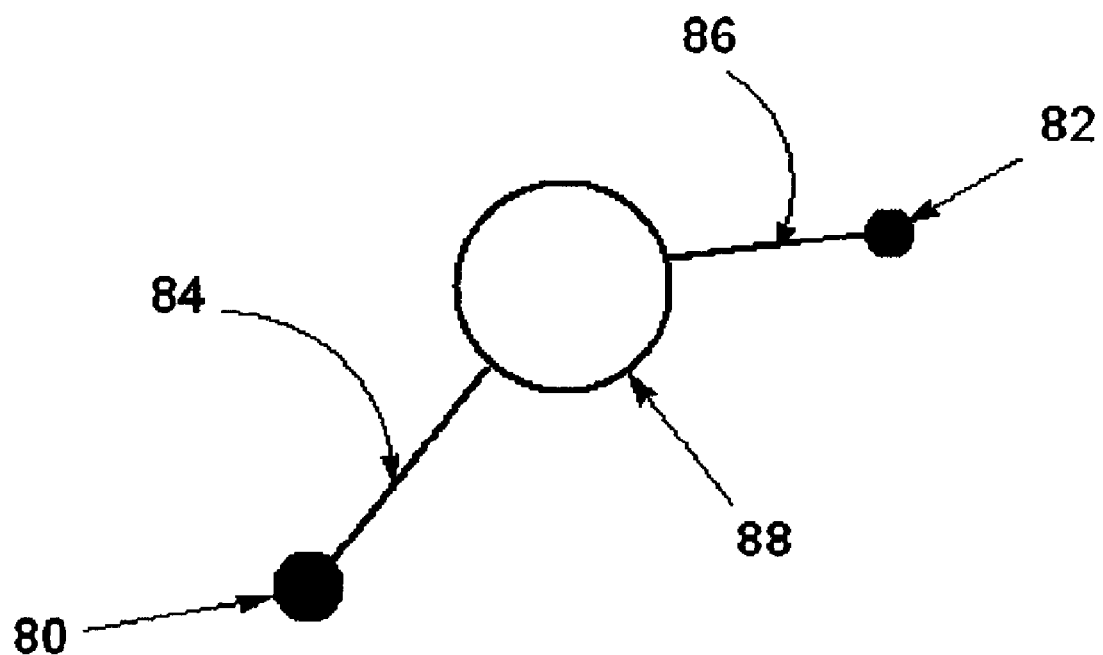
FIG. 5 shows a fragment capped by dummy atoms.

A complication of the strategy described above arises from the fact that conformations of fragments and fragment pairs are actually sampled instead of complete molecules. It may happen that fragment conformations, which are very close in conformational space and thus fall below the RMSD threshold μ, lead to conformations of the complete molecule that are very far apart. In order to deal with that problem, it is advantageous to approximate RMSDs of the complete molecule while sampling conformations on the fragment or fragment pair level. This is done by attaching dummy atoms (or dummy weights) 80, 82 to respective connecting bonds 84, 86 at respective distances of l, l' from the fragment 88 (see FIG. 5). An analogous procedure may be used in the case that the fragment 88 is actually a fragment pair, with the dummy weights 80, 82 being attached to respective fragments in the fragment pair. These dummy atoms 80, 82 can be thought of as representing the average centroid of the remainder of the full molecules which has, for example, N atoms and therefore carries a weight, w=N in the RMSD computations. Choosing l=N/6 Å, which is approximately the distance of the centroid of a stretched hydrocarbon chain of N atoms, has been found to work well. The angular resolution Δφ determines how completely the conformational space is being sampled given the accuracy parameter μ. If Δφ has been chosen to be too large, certain conformations important for the alignment with the query molecule may be missed. A value of Δφ=60° has been found to work well.

1.3 Feature Definition

The query molecule, as well as the fragment pair conformations in the database, is represented by a set of features reflecting local physico-chemical properties of the molecules. These features are explicitly calculated and stored for each fragment pair conformation. A feature F can be written as a tuple $$F=(I, K, x, \underline{p}) \quad (1)$$

where I is an integer representing the feature type, K is a reference to the fragment pair (not present for query features), x is the location of the feature in Cartesian space (in the fragment pair or query molecule coordinate system), and $\underline{p}$ is an optional unit vector that may represent any directional or orientational information of the feature, e.g., the direction of a hydrogen bond. All fragment pair features are stored in a lookup table as a pair (index, value list), in which I serves as the lookup index, and (K, x, $\underline{p}$) represents an entry in the value list.

FIG. 6 presents the definitions of the different SYBYL® (see M. Clark et al., J. Comput. Chem., vol. 10, p. 982, 1989) atom type-based feature types and feature indices that can be used with working examples of the present invention. In some cases the number of bonds is given in angled brackets after the SYBYL® atom type. (See eq. (1) for the definition of the vectors x and $\underline{p}$.) For simplicity, compounds having metal ions are not considered here. Note that there may be more than one feature at a given point. The feature indices are 1 (hydrogen bond donor), 2 (hydrogen bond acceptor), 3 (base group, positive charge), 4 (acid group, negative charge), 5 (hydrophobic), and 6 (hydrophobic-aromatic). All features are located on non-hydrogen atoms except for hydrophobic groups, benzene rings where the ring center is used, and carboxyl groups where features are placed in the middle of the distance between the oxygen atoms.

"Hydrophobic atoms" as defined in FIG. 6 are combined into hydrophobic groups represented by single features. These hydrophobic groups are obtained as connected components of a distance-compatibility graph, in which the vertices correspond to the hydrophobic atoms and an edge is created if the distance between two of those atoms is smaller than a certain cut-off distance, taken here to be 3 Å. The feature location is given by the center of geometry of the atoms within a group.

The information about the group size, i.e., the number of carbon atoms contained within the group, is passed along through the lookup table. In order to make feature matches between two hydrophobic groups more specific, only groups are considered for pattern matching in which the difference in the number of atoms is less than 3. Note that the above definition of hydrophobic groups is inherently conformation-dependent and cannot be derived from molecular topology information alone.

The vector $\underline{p}$ attached to a feature represents either the approximate direction of a fictitious hydrogen bond or, in the case of a benzene ring, the normal to the ring plane. In the latter case, the sign of the vector is not used during processing of the query.

As in the fragmentation and conformational expansion steps (see sections 1.1, 1.2), OH, SH, carboxyl (COO⁻), amine oxide, $SO_3^-$, and $PO_3^-$ groups are treated in a special way. Since the dihedral angle at an OH or SH group is not expanded, both an acceptor and a donor feature are placed on the O or S atom with the vector p pointing in the direction of the bond away from the non-hydrogen atom connected to O or S. The inherent flexibility of a hydroxyl or SH group is accounted for by choosing appropriate angular tolerances (see eq. (7)) in the pattern matching procedure, as discussed below). Carboxyl groups are treated in a similar way. They are treated here as being deprotonated (even if a hydrogen atom is explicitly present in the input file) and therefore carry an acid feature and a hydrogen bond acceptor feature. Flexibility is accounted for here by the choice of the angular tolerance of the attached vector (see below). $PO_3^-$ and $SO_3^-$ groups only carry a charge (acid) feature on the phosphorus or sulfur atom and no features on the oxygen atoms.

1.4 Lookup Table and Pattern Matching

When a database query is launched, lookup table entries are retrieved for each query molecule feature resulting in a list of feature correspondences {c1, c2, . . . }. A feature correspondence c is the match of a single feature on the query molecule with a feature on a fragment pair, i.e., both the query feature and the fragment pair feature have the same feature type (or lookup index). c can be expressed as $$c = (x_q, x_d, \underline{p}_q, \underline{p}_d, K) \quad (2)$$

in which $x_q$ and $x_d$ are, respectively, the feature locations on the query molecule and a fragment pair of a particular database molecule, $\underline{p}_q$ and $\underline{p}_d$ are the corresponding unit vectors encoding directional information, and K is the fragment pair index. Different molecules in the database are preferably processed separately, so that fragment pair conformations belonging to only one molecule at a time are considered.

In order to detect common feature patterns on the query molecule and on a particular fragment pair conformation, it is advantageous to find sets of feature correspondences $$c_j = (x_{qj}, x_{dj}, \underline{p}_{qj}, \underline{p}_{dj}, K_j), j=1, \ldots, V, \quad (3)$$

in which V is the number of votes that can be matched simultaneously within a certain geometric tolerance by aligning the fragment pair onto the query molecule. This alignment can be expressed by a rotation matrix R and a translation vector t applied to the fragment pair. R and t are determined by the condition that $$|x_{qj} - R x_{dj} - t| \text{ and } \angle(\underline{p}_{qj}, R \underline{p}_{dj}) \quad (4)$$

are small given a certain tolerance for all j=1, . . . , V. The alignment of the fragment pair defined by the rotation R and translation t then represents a hypothesis with V votes.

Figure 7:
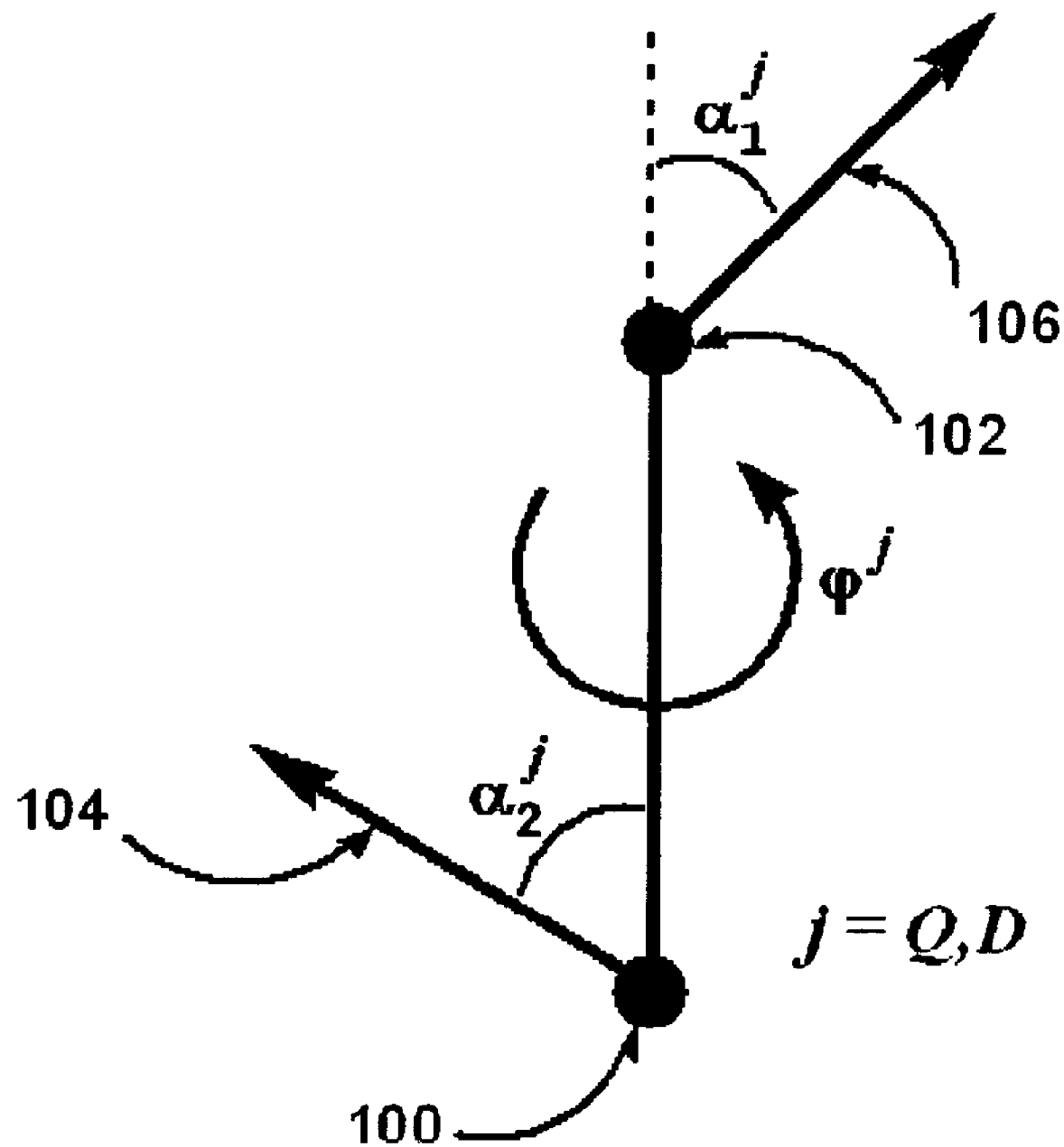
FIG. 7 defines angles between the directions of two features located on a query molecule or a fragment pair conformation of the database.

The pattern matching problem described above can be treated within a clique detection approach by mapping the feature correspondences onto the vertices of a graph G, in which two vertices are connected by an edge if the corresponding feature correspondences are pair-wise compatible. Alignments with V votes then correspond to cliques with V vertices in the graph G. Two feature correspondences (indexed by i=1, 2 in the discussion that follows)

$$c_i = (x_{qi}, x_{di}, \underline{p}_{qi}, \underline{p}_{di}, K_i) \quad (5)$$

are defined to be compatible if the distances between the features are the same on the query molecule and on the fragment pair within a tolerance $\epsilon = \epsilon_1 + \epsilon_2$, $$||x_{q1} - x_{q2}| - |x_{d1} - x_{d2}|| < \epsilon, \quad (6)$$

and a pair-wise alignment $\underline{d}_q \| R \underline{d}_d$ (where R is a rotation matrix) of the difference vectors $\underline{d}_q = x_{q1} - x_{q2}$ and $\underline{d}_d = x_{d1} - x_{d2}$ exists, such that $$\angle(\underline{p}_{qi}, R \underline{p}_{di}) < \gamma_i, \quad (7)$$

in which $\gamma_i$ denotes an angular tolerance. The parameters $\epsilon_1$, $\epsilon_2$, $\gamma_1$, and $\gamma_2$ are independently assigned to the two feature correspondences $c_1$ and $c_2$. It can be shown that eq. (7) is equivalent to the condition $$\Delta\phi_1 + \Delta\phi_2 \geq |\phi^Q - \phi^D| \quad (8)$$

in which $$\Delta\phi_i = 2 \arcsin(\sqrt{\gamma_i}) \quad (9)$$

and $$\lambda_i = [\cos(a^Q_i - a^D_i) - \cos \gamma_1]/2 \sin a^Q_i \sin a^D_i \quad (10)$$

with $\phi^Q$, $\phi^D$, $a^Q_i$ and $a^D_i$ defined as shown in FIG. 7. The points 100, 102 (·) in FIG. 7 denote two features located on the query molecule (j=Q) or a fragment pair conformation in the database (j=D). The arrows 104, 106 are the corresponding vectors $\underline{p}$ (see eq. (1)). If $\lambda_1 < 0$ or $\lambda_2 < 0$, then no pair-wise alignment is possible. Otherwise, if $\lambda_1 \geq 1$ or $\lambda_2 \geq 1$, then a pair-wise alignment is always possible.

Preferred methods herein use an incremental approach to compute the list of all cliques in the graph G ordered by the number of votes. The actual fragment pair alignments or hypotheses—represented by the rotation R and translation t—are then determined by an RMSD minimization procedure applied to the feature locations. While pair-wise distance compatibility of feature correspondences ensures the distance compatibility of the whole feature pattern (except in situations with mirror symmetry), this is not the case for the pair-wise angular compatibility of the attached vectors $\underline{p}_{qj}$ and $\underline{p}_{dj}$. Therefore, after clique-detection a post-processing step is applied that removes all feature correspondences in the clique where $\angle(\underline{p}_{qj}, R \underline{p}_{dj}) \geq \gamma_j$ and reduces the number of votes V accordingly. Note that at least 3 votes are needed for a unique alignment. For this reason all cliques with V<3 are discarded.

In order to limit the workload in the subsequent processing steps not all hypotheses are passed to the assembly procedure. For each fragment pair conformation, hypotheses that pass an additional shape screen (see section 1.2) are ordered with respect to votes, and put into "buckets", $B_k$, containing all hypotheses with the same number of votes, $V_k$. All n buckets $B_k$ with the highest number of votes ($V_1 = V_{max}$; $V_2 = V_{max} - 1$; . . . ; $V_n = V_{max} - n + 1$), in which $V_{max}$ is the maximal number of votes, and $$\Sigma_{k=1,n-1} m_k + m_n/2 \leq p, \quad (11)$$

are handed over to the assembly, where $m_k$ is the number of hypotheses in $B_k$. This ensures that the total number of hypotheses per fragment pair conformation is always smaller than 2p. Unless stated otherwise, p=5 in the examples described below.

1.5 Assembly Algorithm

After lookup and pattern matching, each stored fragment pair conformation results in zero, one, or a plurality of "hypotheses", i.e., fragment pairs that are aligned to the query molecule. A hypothesis can be written as an ordered pair (f, g) of fragments in which $f = \{x_1, x_2, \ldots, x_n\}$ and $g = \{y_1, y_2, \ldots, y_n\}$ are atomic coordinates of the two fragment conformations in the fragment pair aligned to the query molecule. f and g can be expressed in terms of the rotation matrices $R_f$ and $R_g$ that define the rotation of the aligned fragments relative to the fragments $f^0$ and $g^0$ stored in the database, $$f=R_f(f^0-x^0)+x;\ g=R_g(g^0-y^0)+y \qquad (12)$$

in which $x^0$ ($y^0$) is the center of geometry of the stored coordinates $f^0$ ($g^0$), and x (y) is the center of geometry of the fragment f (g) aligned onto the query molecule Q. $R_f$ and $R_g$ can be calculated from the rotation R obtained in the pattern matching step and the known rotations and translations $R^0_{f,g}$ that map the fragment coordinates stored in the database onto fragment pair coordinates.

$$R_f=R*R^0_f;\ R_g=R*R^0_g \qquad (13)$$

Figure 8:
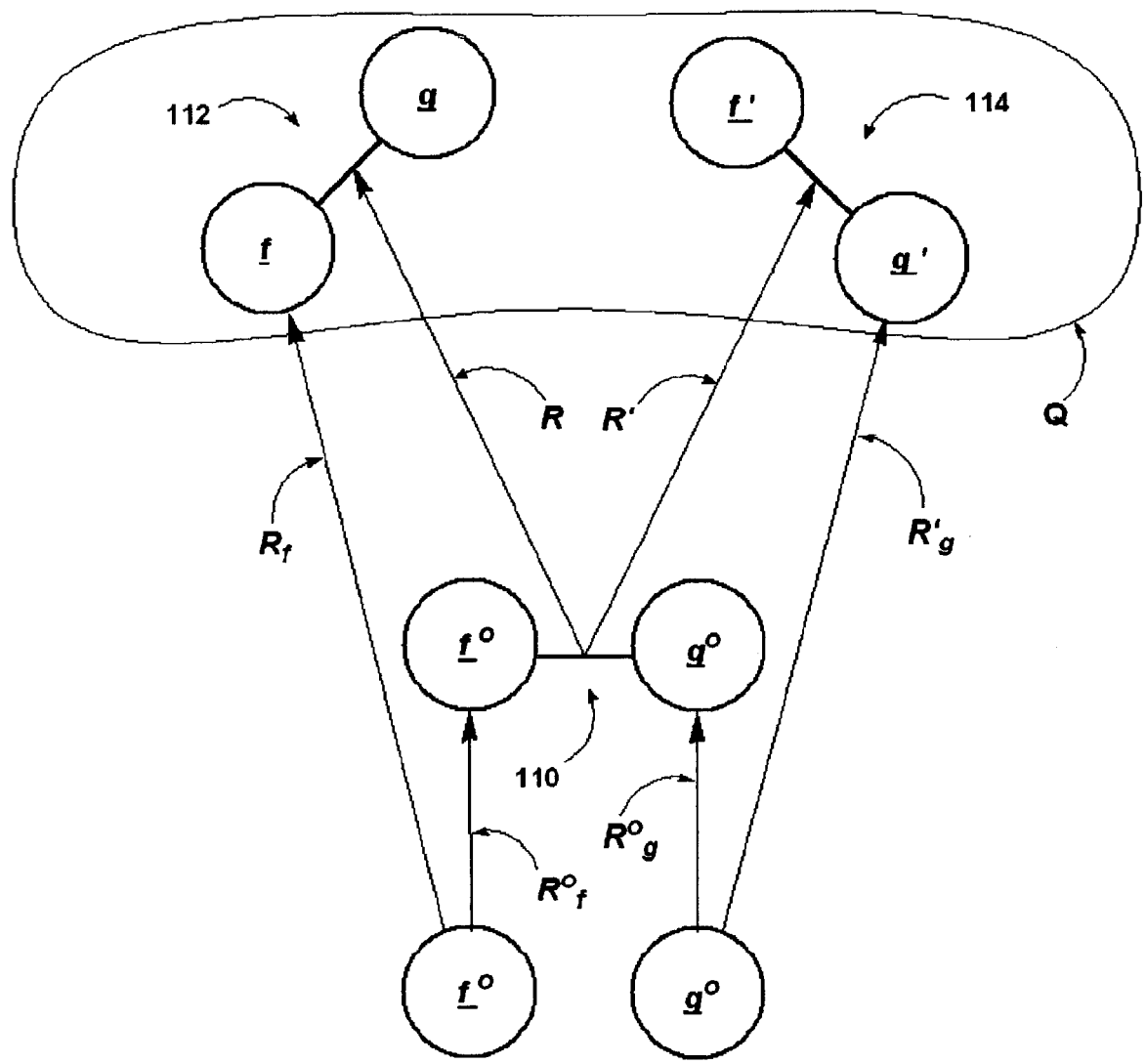
FIG. 8 is a schematic representation of the rotation/translation transformations that map i) fragment conformations onto fragment pairs and ii) fragment pairs onto hypotheses aligned with the query molecule.

These concepts are outlined schematically in FIG. 8, in which the various arrows correspond to the indicated rotation/translation transformations. As shown in FIG. 8, the fragments $f^0$ and $g^0$ undergo respective rotation/translation transformations, thereby forming the fragment pair ($f^0$, $g^0$) 110; this corresponds to the step previously illustrated with respect to FIGS. 1A and 1B. The query procedure generates rotation/translation transformations R, R' which align the fragment pair ($f_0$, $g^0$) onto the query molecule Q, thereby producing two hypotheses (f,g) 112 and (f',g') 114 that are aligned onto the query molecule Q.

The goal now is to find all candidates, i.e., superpositions of a complete database molecule with the query molecule, which are consistent with the hypotheses. This can be viewed as looking for sets of hypotheses $$H_1=(f_1, f_2), H_2=(f'_2, f_3), \ldots, H_{N-1}=(f'_{N-1}, f_N) \qquad (14)$$

in which the coordinates of overlapping fragments are sufficiently close with respect to a certain metric d (defined below). Here N is the number of fragments present in the molecule, and $f_i$ and $f'_i$ stand for the same fragment conformation, but with different coordinates according to the alignments of the hypotheses $H_{i-1}$ and $H_i$. For the assembly procedure, the following metric d in the space of the coordinate representations of a fragment conformation f is used:

$$d(f,f')=\tfrac{1}{2}|y_f-y_{f'}|+a/2\ a\ \cos[\tfrac{1}{2}Tr(R_f R_{f'}^T)-1] \qquad (15)$$

d consists of a translational part and a rotational part. The translational part is simply the distance of the centers of geometry of f and $f^0$, while the rotational part represents the angle of rotation between f and $f^0$. The parameter a determines the relative weight of both contributions and is chosen to be a=3 Å (see M. C. Pitman et al., J. Comput. Aided Mol. Des., vol. 15, p. 587, 2001). Note that explicit coordinates are not needed in order to evaluate d.

The candidate assembly can be expressed in terms of a graph representation, in which hypotheses form the vertices of a directed graph G and two hypotheses are connected by a directed edge (f, g)→(g', h) if the distance (in terms of the metric d, see eq. (15)) of the overlapping fragment g, g' is smaller than a cutoff parameter δ, $$d(g, g')<\delta \qquad (16)$$

i.e., (f, g) and (g', h) are pair-wise compatible. A good working value of δ is 2 Å.

A candidate then corresponds to a directed path of length N in the graph G. In the assembly procedure, all those paths in G are enumerated that can be done in a straightforward way using recursion. Since the number of votes every fragment receives as a result of "matching" is known, the total number of votes for candidates can be calculated by adding up all votes along the path. Votes of overlapping fragments are weighted by a factor of ½ to avoid counting them twice.

Figure 9:
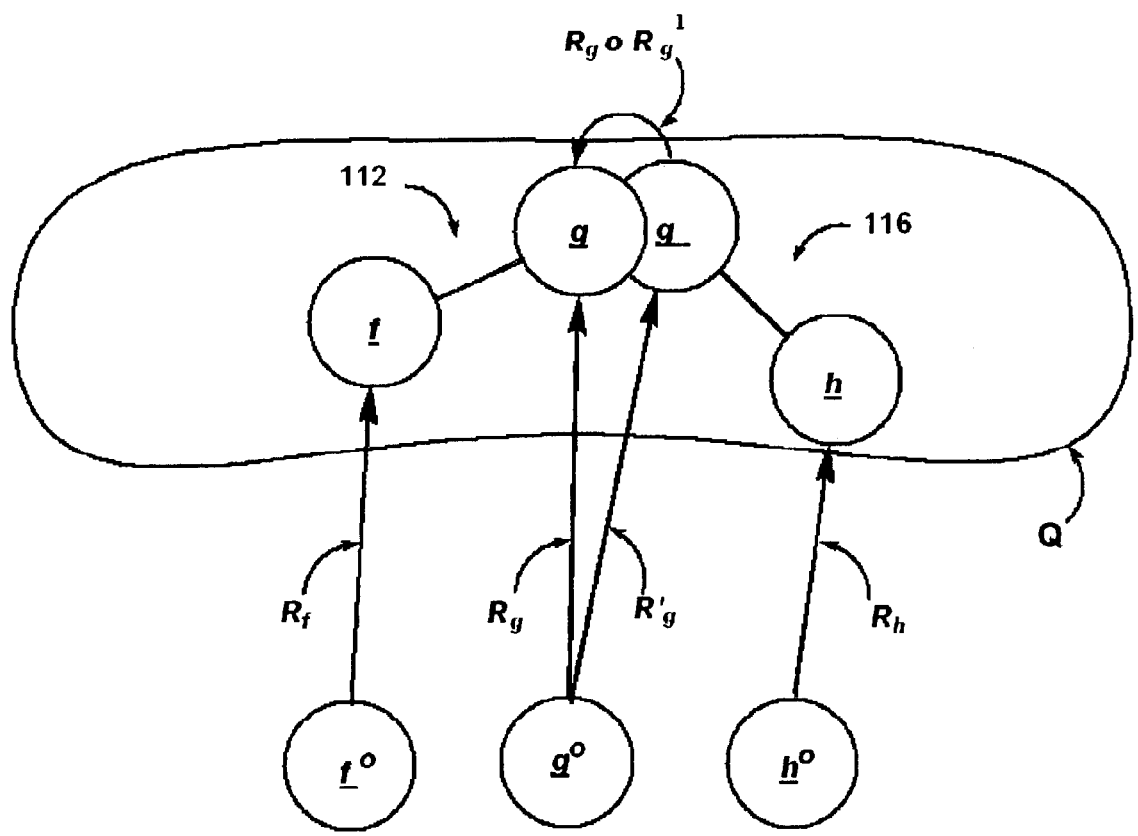
FIG. 9 is a schematic representation of the merging of pair-wise compatible hypotheses that are aligned to the query molecule.

The result of this graph-based assembly procedure is a list of candidates, which is ordered by the number of votes, and in which each candidate is represented by a path in G. In order to obtain the explicit coordinate representation of a candidate, fragments are explicitly rotated and translated. This is done by starting from the first fragment $f_1$ and then "adding" the other fragments successively. All rotations and translations needed in this process can be calculated straightforwardly from the rotation matrices and centers of geometry, which were used above to calculate the distance d of adjacent hypotheses. The process of merging pair-wise compatible hypotheses is outlined schematically in FIG. 9. In order to "add" fragment h from hypothesis (g', h) 116 to hypothesis (f, g) 112, where the compatibility condition given by eq. (16) is satisfied, the rotation/translation transformation $R_g*R_{g'}^{-1}$, is applied to the coordinates of the fragment h.

After the assembly of a candidate in Cartesian space, a rigid alignment to the query molecule is performed using RMSD minimization with respect to the matching feature points. Of course, the explicit calculation of candidate coordinates is an expensive procedure. Thus, it is advantageous to do an explicit assembly only for the highest scoring candidates that do not fail a bump check (see section 1.2) and pass an additional shape screen (see section 2). For this set of candidates, which represent the final result of the query, the Carbo score is also calculated. (See R. Carbo et al., Int. J. Quant. Chem., vol. 17, p. 1185, 1980; in preferred implementations of the invention the Carbo function is used with three-dimensional Gaussian densities exp $(-(r-\underline{r}_0)^2/2\tau^2)$, in which $\underline{r}_0$ is an atom center and τ=1 Å, as described in M. C. Pitman et al., J. Comput. Aided Mol. Des., vol. 15, p. 287, 2001.)

2. Examples

Two types of examples are presented that are designed to assess the performance of the algorithm (in terms of CPU time), the quality of molecular alignments, the influence of the sampling resolution of the conformational space, and the sensitivity and selectivity of the molecular similarity search method. The first type is a mutual alignment of pairs of molecules that bind to the same receptor, and in which conformations of the bound states are known (see section 2.2). In a second type of example, queries are performed against a database of 1780 compounds comprising 52 known dihydrofolate reductase inhibitors (methotrexate, dihydrofolate (which served as the query molecule), and 50 molecules from the dataset of Crippen et al., J. Med. Chem., vol. 23, p. 599, 1980—in particular, compounds 2, 3, 4, 5, 6, 7, 8, 9, 10, 11, 12, 13, 15, 16, 17, 18, 19, 21, 22, 23, 24, 25, 29, 30, 31, 32, 34, 35, 36, 38, 39, 41, 42, 43, 45, 46, 47, 48, 49, 50, 52, 54, 56, 57, 60, 62, 63, 64, 65, 66 from this reference—see FIG. 13) as well as 1728 compounds taken from the diversity set of the National Cancer Institute (NCI) (see the Internet website identified by the concatenation of "http://" and "dtp.nci.nih.gov/docs/3d database/structural information/structural data.html"). Throughout these examples, a feature definition is used that is based on SYBYL® atom types (see M. Clark et al., J. Comput. Chem., vol. 10, p. 982, 1989 and FIG. 6).

Parameters used in these examples are $\epsilon_i$=0.4 Å for the distance tolerance (eq. (6)), except for hydrophobic groups, for which $\epsilon_i$=0.7 Å if the matching groups both contain only one atom and $\epsilon_i$=1.5 Å otherwise. The angular tolerance (eq. (7)) is $\gamma_i$=50°, except for the special cases of carboxyl and hydroxyl-like groups, where γ was chosen to be 90° to reflect the internal flexibility. The cutoff parameter for the assembly of adjacent hypotheses (eq. (16)) was set to δ=2 Å. The shape screen imposed before and after assembly removes all hypotheses and candidates that contain an atom farther than 4 Å away from any atom of the query molecule.

2.1 Scoring

In the examples herein, a generalized scoring scheme is used (as opposed to just counting votes) to allow for different weights of feature correspondences depending upon the type of feature involved. This was done in order to better balance the importance of the various functional groups in the calculation of the score. For instance, a match between two carbonyl groups (>C=O) with two hydrogen bond acceptors are taken to have weights different from that of two independent hydrogen bond acceptors. Similarly, a match between two carbonyl groups is preferably weighted higher than a match between a carbonyl group and some single hydrogen bond acceptor. All weights were chosen to be equal to 1 except for double tetrahedral and double planar acceptors, and hydroxyl-like donors and acceptors, in which the weight was set equal to 0.86. The "votes score" is then defined as $$\text{votes score} = (\Sigma_{feature\ correspondences}\ w_q\ w_d)/(\Sigma w_q^2)^{1/2} (\Sigma w_d^2)^{1/2} \quad (17)$$

Here $w_q$ and $w_d$ are the weights of features on the query molecule Q and the candidate D under consideration, and the sums in the denominator run over all features on Q and D. Note that the votes score as defined above is a number between zero and one. The introduction of feature type-dependent weights requires the additional information about a specific feature type to be passed along in the lookup table. This also allows for a feature type-dependent definition of distance and angular tolerances used in the pattern-matching algorithm (see Eqs. (6) and (7)).

2.2 Molecular Superposition

Mutual superpositions have been performed for a test set of 19 molecules (ligands) known to bind to one of 7 different receptors (proteins) for which the crystal structure of the protein-ligand complex is available, and from which the "correct" molecular alignment can be inferred (see C. Lemmen et al., J. Med. Chem., vol. 41, p. 4502, 1998). These molecules (listed in FIG. 10) are all medium-sized compounds taken from the FlexS™ benchmark set (see C. Lemmen et al. on the Internet website identified by the concatenation of "http://" and "www.biosolveit.de", and C. Lemmen, J. Med. Chem., vol. 41, p. 4502, 1998). These examples demonstrate the ability of preferred methods of the invention to handle molecular flexibility in an efficient manner. Accordingly, small, rigid molecules are not considered herein, because they represent trivial cases for the flexible pattern matching procedure. For all molecules in the test set that fall into the same receptor class, mutual "rigid" superpositions were performed, in which the fragmentation-reassembly procedure was bypassed and only the crystallographically known structure of one ligand was put into the database. The correct alignments (as specified in the FlexS™ benchmark set) were produced with an accuracy of less than 1.5 Å RMSD (with respect to non-hydrogen atoms) for all pairs of molecules except for some cases of H. rhinovirus coating protein ligands, for which a reverse orientation of the molecules was found (see Example 2). In most cases the alignment was better than 0.7 Å RMSD, demonstrating the suitability of the atom type-based feature definition for the set of molecules considered here. The vote scores for these "rigid" superpositions are listed in the next-to-last column of FIG. 10, and the last column shows the ratio between the "flexible" vote scores obtained from queries (described next) and the "rigid" vote scores. For self-queries, values less than or equal to 1 are expected; deviations indicate less-than-perfect conformational sampling. Values greater than 1 for non-self-queries indicate the importance of taking molecular flexibility into account.

In the next step, databases were prepared, each of which contains fragment pair conformations of one molecule from the test set. During the conformational sampling procedure, to ensure that the molecular conformation that corresponds to the crystal structure was not contained in the database, random offsets in the dihedral angle expansion were added. This ensures that self-queries, for which the query and database molecules are the same, are non-trivial, and can be used as a test of how well the conformational space is being sampled. All dihedral angles were sampled with a resolution of $\Delta\phi=60°$, except for the case of 7cpa (a carboxypeptidase A inhibitor), for which a correct self-alignment (<2.4 Å RMSD) could only be achieved with $\Delta\phi=30°$. The molecular partitioning scheme (see section 1.1) was optimized for each molecule in the sense that the number of stored fragment pair conformations was made as small as possible, while the fragment pairs were still large enough to allow for a complete assembly. Databases generated this way were queried with all molecules in the test set that bind to the same receptor as the database molecule. As seen in FIG. 10, most of the molecules have been partitioned into 3 fragments or 2 fragment pairs. Only in the case 1dwc vs. 1dwd (row 3 in FIG. 10) could fully assembled candidates be obtained from 3 fragment pairs for a non-self query. In this case, the parameter p (see eq. 11) was set equal to 7 in order to collect enough hypotheses. In FIG. 10, "R" refers to a reverse alignment of the query and database molecules. An "X" means that no candidate was found. The CPU times shown were obtained on a PC with a 1.8 GHz Pentium 4 processor.

FIG. 10 summarizes the results of the mutual molecular superpositions. Candidates were first ordered by the votes score and then by Carbo score for candidates with identical votes score. Votes score, Carbo score, and the RMSD with respect to the correct alignment are shown for the highest scoring candidate. The smallest RMSD value out of the 10 highest scoring candidates is also given in brackets.

Figure 11:
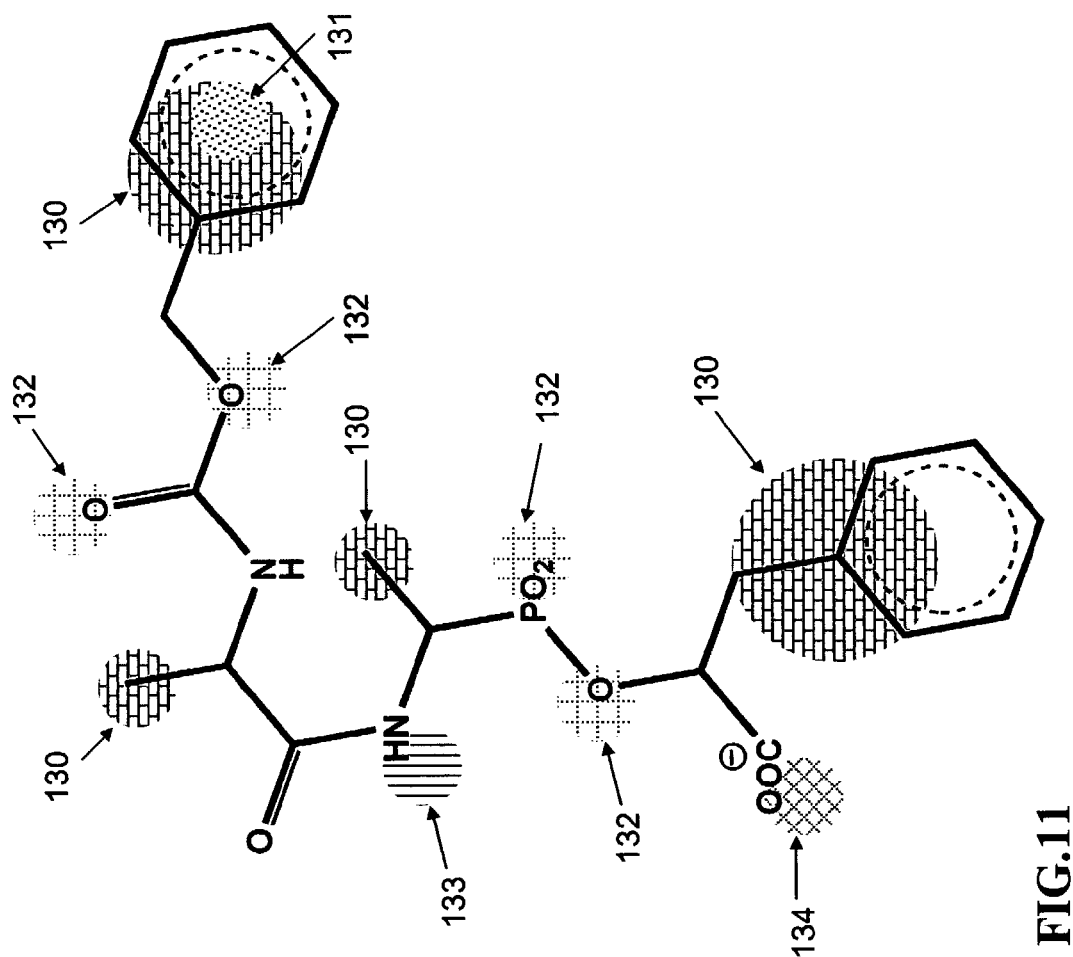
FIG. 11 shows the result of the self-query for the carboxypeptidase A inhibitor 6cpa.

FIG. 11 shows the result of a self-query of the carboxypeptidase A inhibitor 6cpa. The molecule had been partitioned into two fragment pairs, which reduces the original number of conformations screened in the dihedral angle expansion from $3.6 \times 10^8$ to 384 explicitly stored fragment pair conformations. The correct molecular alignment is obtained within an accuracy of 1.37 Å RMSD, and almost all possible feature correspondences are found despite the fact that the exact conformation of the query molecule was not contained in the database. This indicates that a torsional angle resolution of $\Delta\phi=60°$ is obviously sufficient for molecules of this size. The shaded areas in FIG. 11 represent different features responsible for matches in the 6cpa self-query. The following reference numerals are used for the various feature types: 130 (hydrophobic), 131 (hydrophobic aromatic), 132 (hydrogen bond acceptor), 133 (hydrogen bond donor), and 134 (negative charge).

It is reasonable to expect that larger molecular structures require smaller values of $\Delta\phi$ in order to avoid the possibility that important molecular conformations are missed. As mentioned above, the largest molecule considered here (7cpa with 74 atoms) is the only structure that required setting Δϕ=30° in order to obtain the self-alignment correctly.

EXAMPLES OF MOLECULAR SUPERPOSITION

The results of FIG. 10 are now discussed in more detail with respect to Examples 1-8, which are not of the self-query type.

Example 1

Thrombin Inhibitors

The ligands 1dwc and 1dwd are of similar size (71 and 69 atoms, respectively), have functionally similar structure elements (guanidine vs. benzamidine), but have backbones of rather different topologies. Convincing mutual alignments were found between 1dwd and 1dwc with minimum RMSDs of 1.93 and 2.28 Å, which are not simple substructure matches.

Figures 12A, 12B:
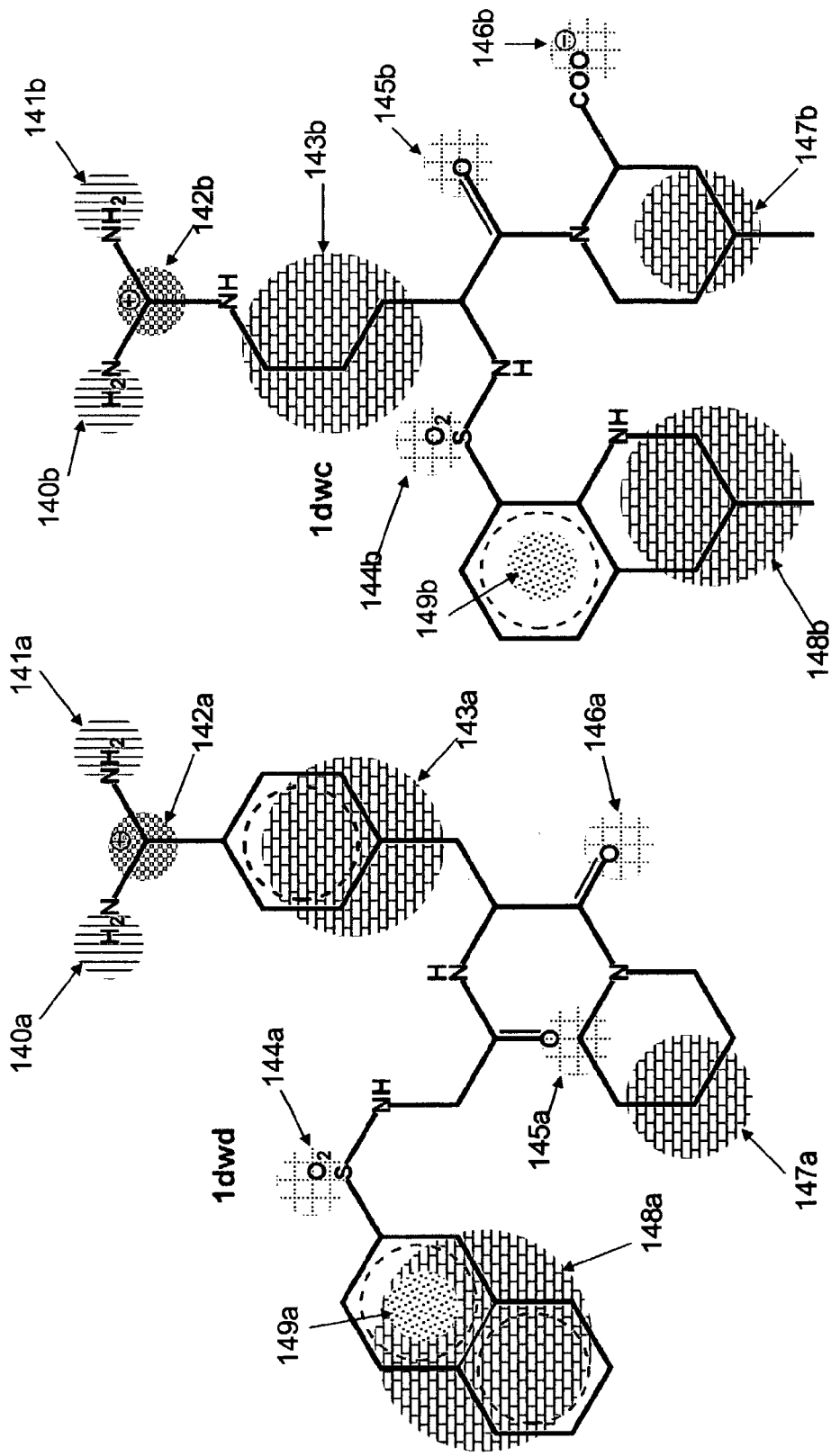
FIGS. 12A and 12B, shows the molecular superposition of the thrombin inhibitors 1dwd and 1dwc, respectively.

FIGS. 12A and 12B show the ligands 1dwd and 1dwc, respectively, in which 1dwd served as the query molecule and 1dwc was stored in the database. Features leading to feature matches between these two molecules are shown. Feature matches are indicated between 140*a*, 140*b* (hydrogen bond donor); 141*a*, 141*b* (hydrogen bond donor); 142*a*, 142*b* (positive charge); 143*a*, 143*b* (hydrophobic); 144*a*, 144*b* (hydrogen bond acceptor); 145*a*, 145*b* (hydrogen bond acceptor); 146*a*, 146*b* (hydrogen bond acceptor); 147*a*, 147*b* (hydrophobic); 148*a*, 148*b* (hydrophobic); and 149*a*, 149*b* (hydrophobic aromatic). For this alignment, the votes and Carbo score were 0.68 and 0.80, the RMSD with respect to the crystal structure was 2.42 Å, and the query processing took 2.2 s CPU time.

Example 2

Human Rhinovirus Coating Protein Ligands

All 4 ligands considered are structurally very similar and include a stretched, flexible hydrocarbon chain capped with two 5-ring heterocyclic termini. The ligands fall into two groups representing binding modes, which differ by a reverse orientation of the entire molecules. Excellent alignments (<1.7 Å) were found between ligands having the same binding mode.

For the case in which 2rs3 was stored in the database, votes and Carbo score for this alignment were 1.0 and 0.93, respectively, the RMSD with respect to the crystal structure was 2.16 Å, and the query processing took 1.8 s CPU time.

Example 3

Fructose Biphosphatase Inhibitors

The chemical structures of these two ligands consist of an N-heterocyclic system bound to a sugar phosphate backbone. The alignments found show a substructure match on the backbone and a non-trivial match involving a reverse orientation of the 5-rings present in both structures (purine in 4fbp and imidazole in t0039) with an RMSD of <0.6 Å.

For the case in which 4fbp was stored in the database, votes and Carbo score for this alignment were 0.63 and 0.96, the RMSD with respect to the crystal structure was 0.57 Å, and the query processing took 0.2 s CPU time.

Example 4

Dihydrofolate Reductase (DHFR) Inhibitors

The ligands dihydrofolate (1dfh) and methotrexate (4dfr) have a pteridine substructure in common that participates in the ligands' binding modes. The correct relative orientation of these substructures resulting from the match of the characteristic hydrogen bond donor/acceptor pattern was found. The overall minimum RMSDs range between 1.54 and 2.30 Å. These relatively large values reflect the fact that all features on the molecule, including those on the hydrophilic tail, are assumed to be of equal importance. The method therefore interpolates between the pteridine ring pattern match and the matches of the benzene ring and the carboxyl groups for the overall superposition, while in reality the alignment of the molecules is determined mainly by the pteridine ring match.

For the case in which 1dfh was stored in the database, votes and Carbo score for this alignment were 0.70 and 0.87, the RMSD with respect to the crystal structure was 1.73 Å, and the query processing took 0.1 s CPU time.

Example 5

Thermolysin Inhibitors

These 4 ligands all possess a similar binding mode, but are very different in size. All queries against 1tlp (especially the self-query) suffer a performance toll from a high load of hypotheses caused by the sugar substructure (which is only present in 1tlp) with its many hydrogen bond donors and acceptors. The (non-self) queries of the smallest ligand 2tmn (26 atoms) against the larger molecules pose a problem because of the size mismatch—no candidates are produced because of missing hypotheses.

For the case in which 3tmn was stored in the database, votes and Carbo score for this alignment were 0.58 and 0.76, the RMSD with respect to the crystal structure was 1.36 Å, and the query processing took 0.1 s CPU time.

Example 6

Carboxypeptidase Inhibitors

The 3 ligands 1cbx, 6cpa, and 7cpa are of very different size (25, 58, and 74 atoms) but all are chemically and structurally similar, with 1cbx being a substructure of 6cpa, and 6cpa being a substructure of 7cpa. Again, no candidates are found in queries of the smaller ligands against the larger ones because of the size mismatch. Queries of the bigger ligands 6cpa, and 7cpa suffer a performance toll from a high load of hypotheses caused by matches on unspecific regions of the molecules such as amide and benzyl groups.

The query of the largest structure 7cpa against 6cpa produces excellent alignments with a best minimum RMSD of 1.39 Å. In this case, 6cpa was stored in the database, and votes and Carbo score for this alignment were 0.67 and 0.81, the RMSD with respect to the crystal structure was 1.60 Å, and the query processing took 10.6 s CPU time.

Example 7

Elastase Inhibitors

The ligands 1ela and 1ele are both of a peptidic nature and possess similar binding modes, with 1ele being primarily a substructure of 1ela with minor variations in backbone substituents. All alignments (self and mutual) obtained are excellent with minimum RMSDs ranging from 0.89 to 1.22 Å.

For the case in which 1ela was stored in the database, votes and Carbo score for this alignment were 0.83 and 0.92, the RMSD with respect to the crystal structure was 1.98 Å, and the query processing took 2.2 s CPU time.

An inherent asymmetry in mutual molecular alignments is exhibited with respect to the size of the structures. The query molecule should be larger than or approximately equal in size as the database molecule; otherwise certain candidates can not be assembled since hypotheses are missing. Substructures or approximate substructures are found only if the substructure itself is the database molecule. This becomes apparent in Examples 5 and 6 above. The CPU times for query processing ($9^{th}$ column of FIG. 10) are in most cases very encouraging, being mostly of the order of a few seconds, in many cases even only fractions of a second. Factors contributing to a slower performance are of course the number of conformations that have to be processed, and also the size of the matching patterns. Self-queries generally take a longer time than mutual superpositions. Many relatively unspecific feature correspondences (see the sugar rest of 1tlp in Example 5) drastically slow down the clique detection algorithm since the underlying graph (see section 1.4) exhibits more edges. An almost ideal case is the methotrexate-dihydrofolate alignment with its very specific, rigid pattern match on the pteridine ring. This, together with the relatively small number of fragment pair conformations that have to be stored, leads to a very short processing time of about 0.1 seconds.

2.3 Database Searches

Figure 13:
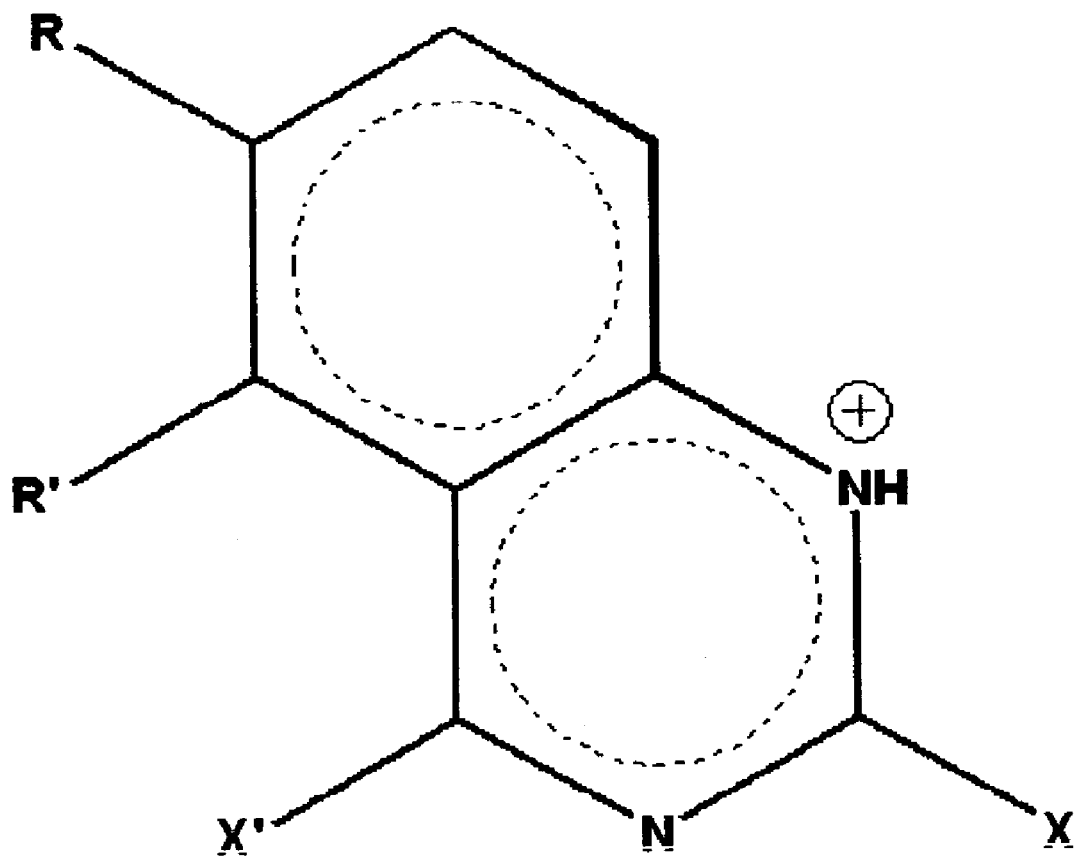
FIG. 13 shows the general structure of the DHFR inhibitors from the dataset of Crippen et al.

Queries have been performed against the test database of 1780 molecules described above. The general structure of the molecules taken from Crippen et al. (J. Med. Chem. Vol. 23, p. 599, 1980) is shown in FIG. 13, in which X=$NH_2$, OH, SH, H, or other substituents; X'=$NH_2$, OH, SH, or other substituents; R=$SO_2$-napht, S-napht, or other substituents; and R'=H, $CH_3$, or other substituents.

All the database molecules were partitioned by an automatic procedure based on the partitioning algorithm described in section 1.1. The total number of fragment pair conformations, which were explicitly stored, was 32872. Database preprocessing, which includes the generation and storage of all fragment pair conformations from an arbitrary starting conformation for each molecule, as well as feature computation and creation of fFLASH's central lookup table, took about 35 minutes.

Figure 14A:
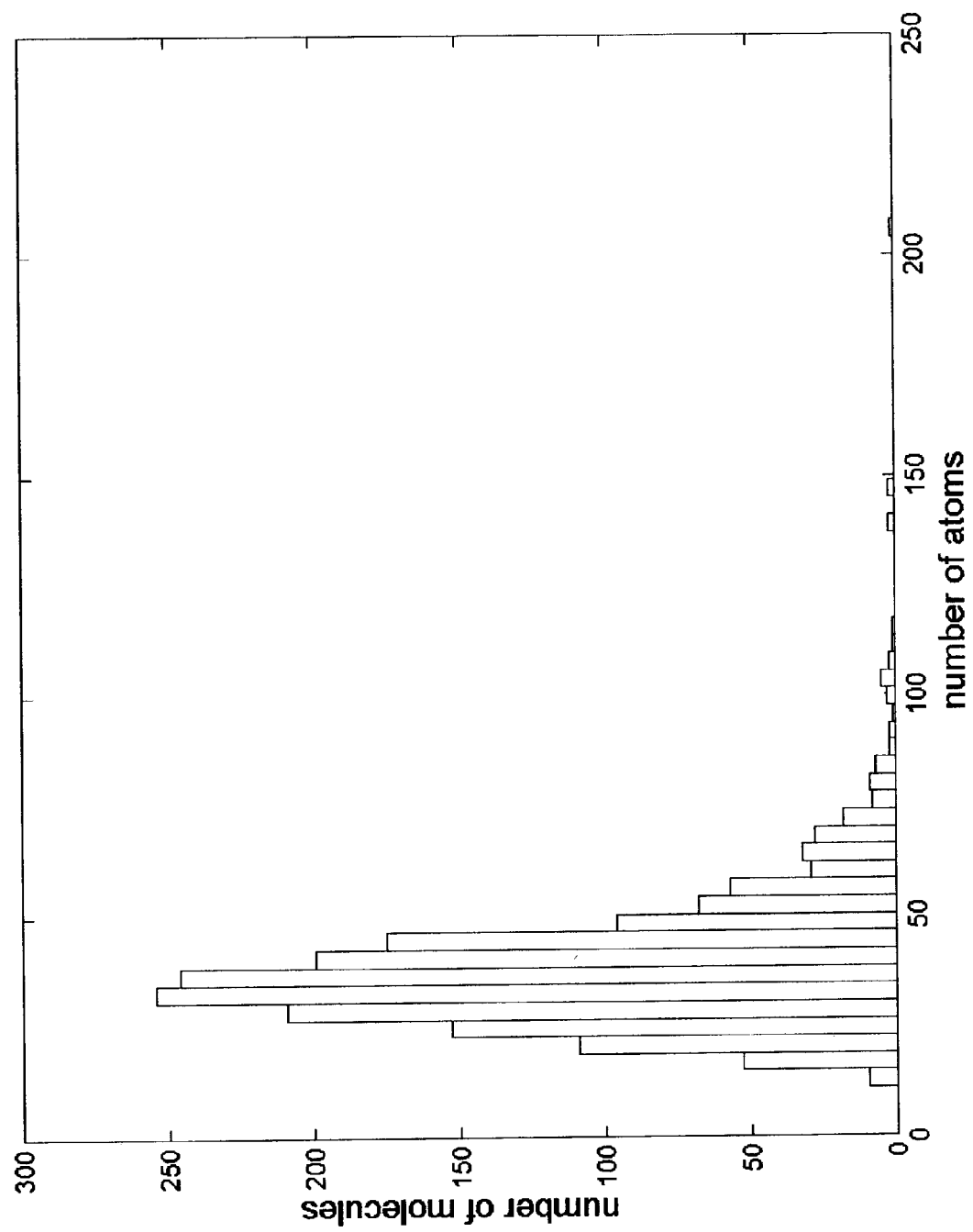
FIG. 14 characterizes the NCI diversity set used as a test database and includes FIGS. 14A, 14B, and 14C, which show, respectively: the distribution of the number of atoms per molecule; the distribution of the number of conformations per molecule; and the distribution of the number of features per molecule.
Figure 14B:
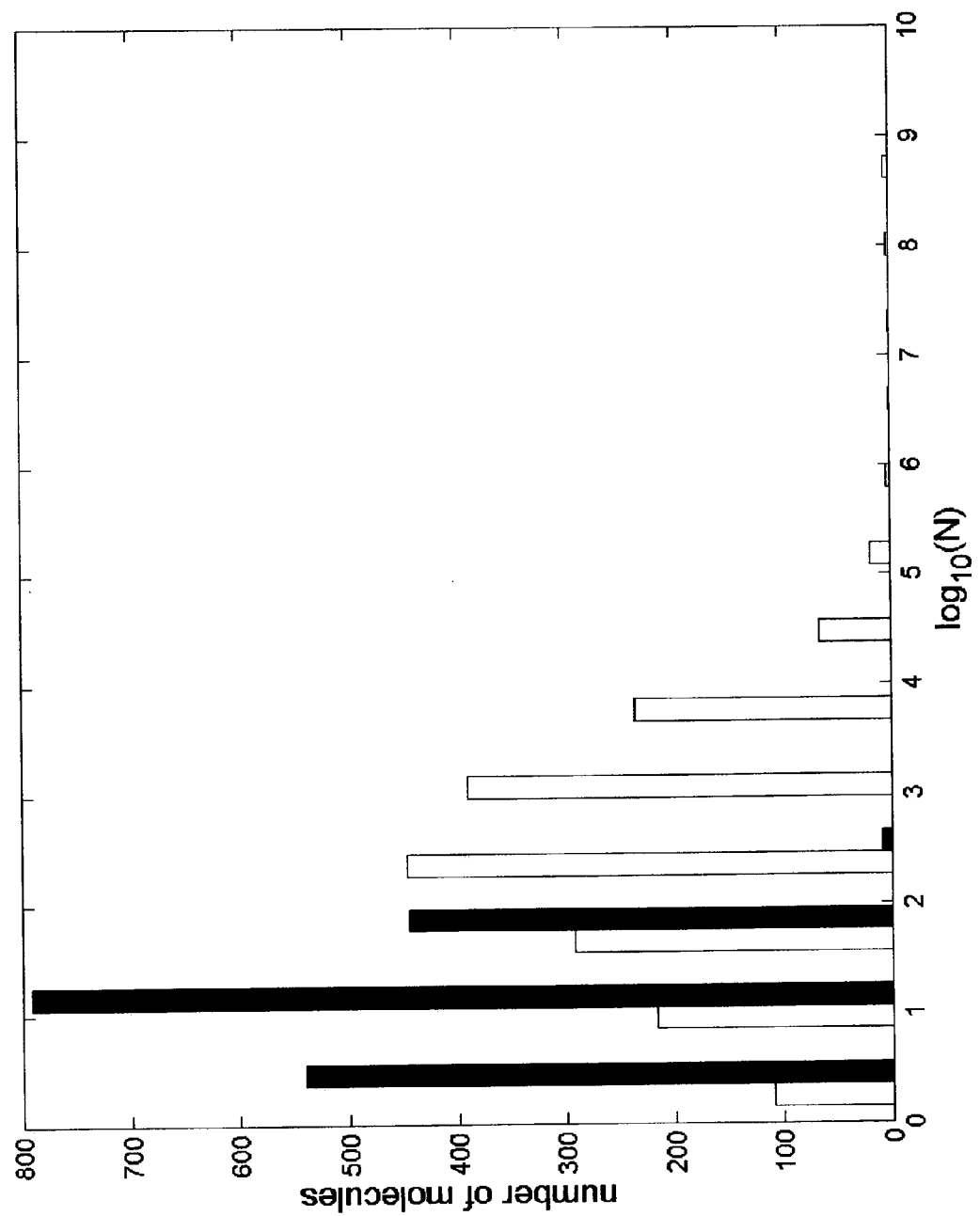

The size distribution of the molecules selected from the NCI database (i.e., the number of atoms per molecule) is given in FIG. 14A, and the distribution of the number of molecular conformations per molecule is shown in FIG. 14B, in which the white bars represent the number of conformations after dihedral angle expansion with $\Delta\phi=60°$, and the black bars represent the number of stored fragment pair conformations. Among the 1728 compounds of the NCI diversity set, there are 1156 that consist of 1 fragment pair, 554 molecules that are partitioned into 2 fragment pairs, 15 molecules with 3 fragment pairs, and 3 molecules with 4 fragment pairs. FIG. 14B distinguishes between the number of conformations obtained from the uniform dihedral angle expansion, and the number of fragment pair conformations explicitly stored in the database. It clearly illustrates the performance impact of the "coarse graining" scheme (see section 1.2) for sampling the conformational space: in the best case, a $10^6$ fold savings in the number of conformations stored is achieved.

Figure 14C:
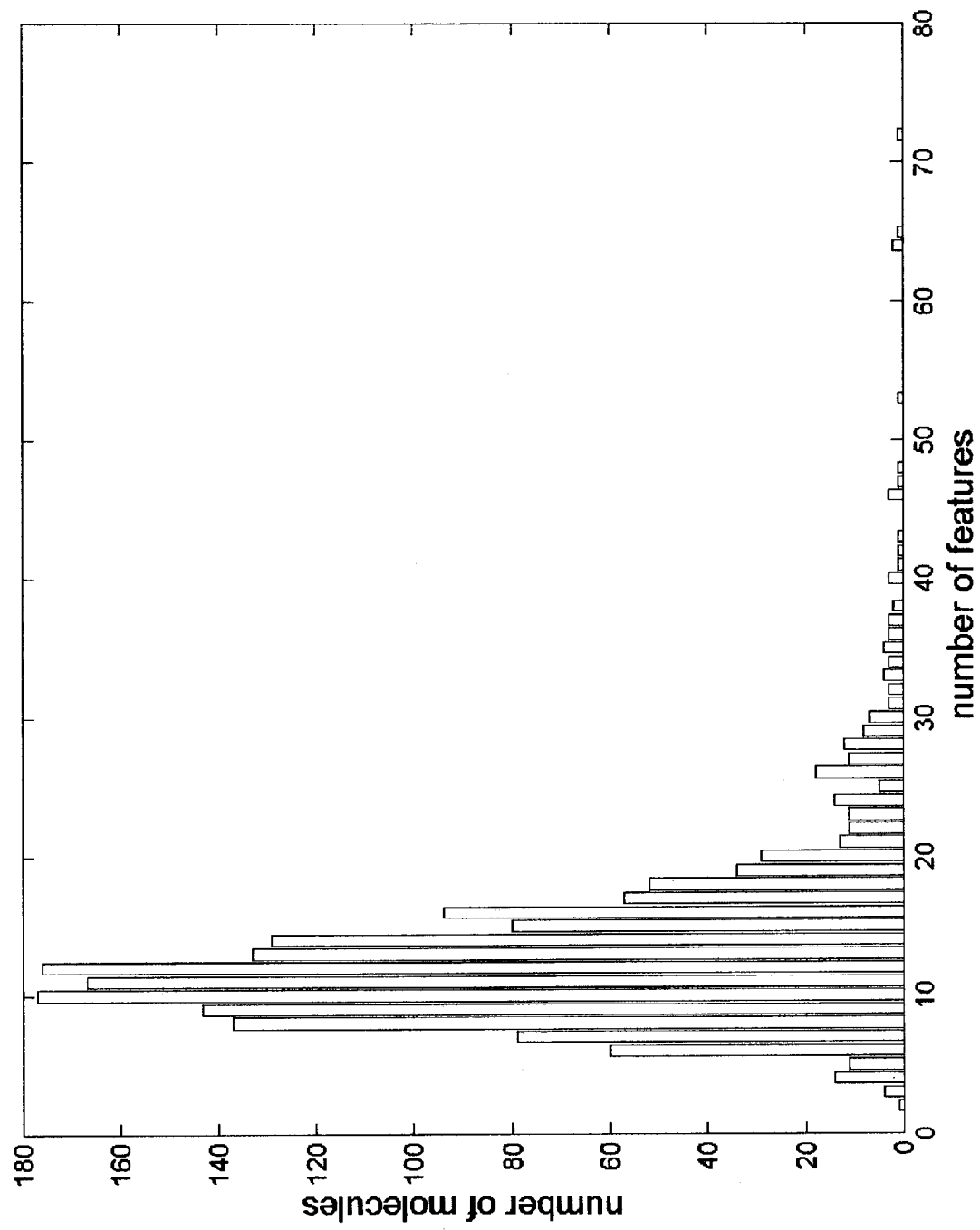

FIG. 14C shows the distribution of the number of features per molecule.

Figure 15A:
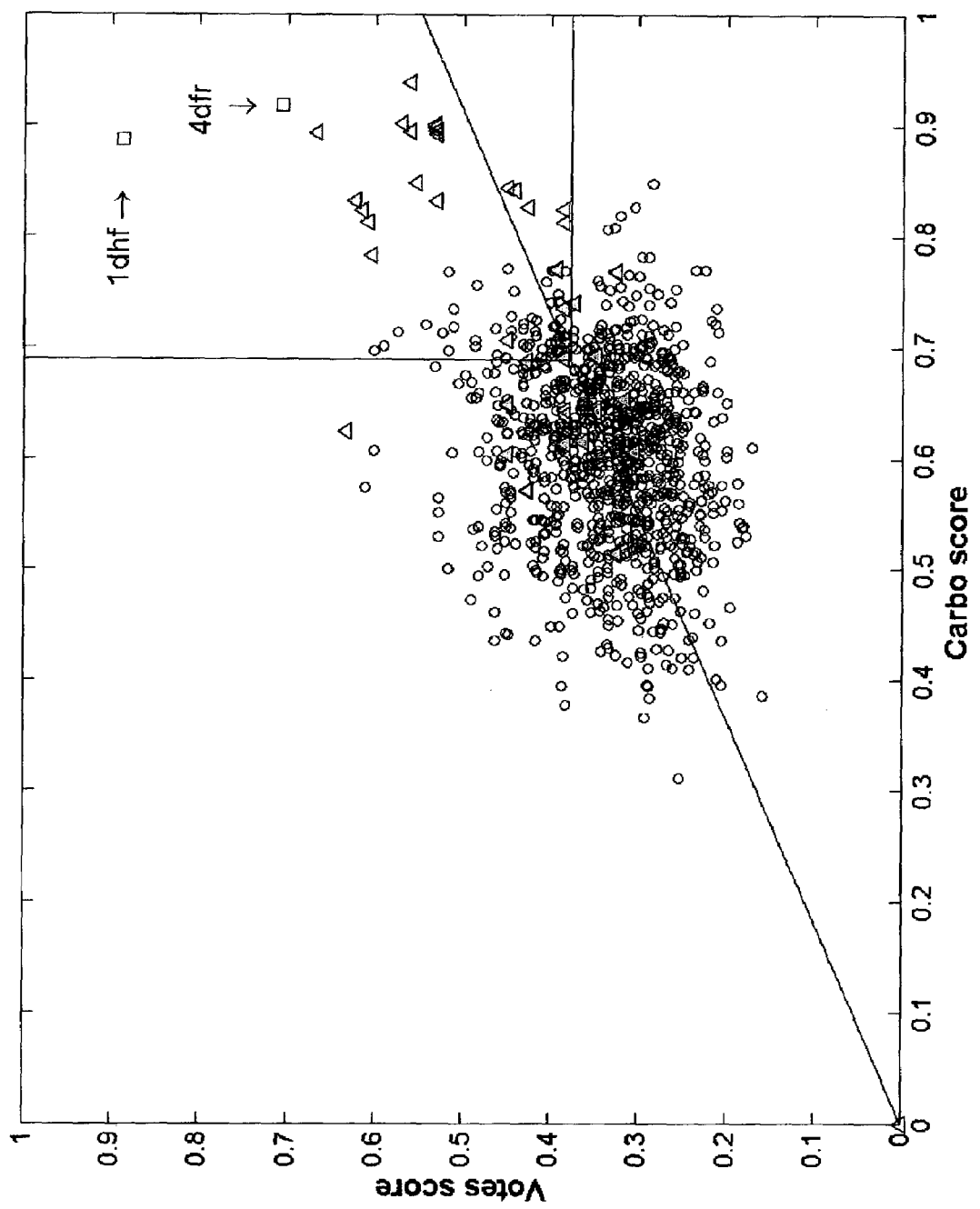
FIG. 15 shows the results of a dihydrofolate (1dfh) query against the test database; it includes FIGS. 15A, 15B, and 15C, which show, respectively: the Carbo and votes scores of the highest scoring candidate for each molecule that passes the assembly phase; the percentage of hits as a function of the Carbo score cutoff value for the NCI diversity set (continuous line) and for the DHFR inhibitors (broken line); and an ROC (receiver-operator curve) plotting the true vs. the false positive hits.

FIG. 15A shows the votes scores and Carbo scores of the highest scoring candidate for each database molecule using dihydrofolate (1dfh) as the query molecule. In this example, the total query processing time was approximately 3 minutes, i.e., on average 0.1 s per database molecule. The points in FIG. 15A represent the molecules from the NCI diversity set, while triangles correspond to DHFR inhibitors from Crippen's dataset. Dihydrofolate and methotrexate are shown as squares. 45% of the database molecules (including 6 DHFR inhibitors) are not shown in the plot since they do not get enough support to be assembled as candidates. Visual inspection of the query results shows that dihydrofolate (self query) and methotrexate, as well as about 50% of the other DHFR inhibitors, receive the highest votes and Carbo scores, and are clearly separated from the "background noise" produced by the NCI diversity set. Reference examples using other query molecules (see FIG. 16) did not alter the location of the point cloud from the diversity set, indicating that the statistics of the background noise in the score plot (see FIG. 15A) are independent of the particular query molecule. Of course, the query processing time strongly depends on the size of the query molecule (or more precisely, the number of its features). The average processing time per database molecule is shown for a number of different query molecules in FIG. 16.

A quantitative analysis of the score plot (see FIG. 15A) can be done by noting that the votes score roughly correlates linearly with the Carbo score for the diversity set, so that a least squares fit is performed with a linear function for the corresponding points. This is the straight line with slope 0.55 in FIG. 15A. "Hits" of a database query, i.e., those molecules considered to be similar to the query molecule, should fall close to the upper right corner of the plot. A rectangle in FIG. 15A has been constructed with sides parallel to the coordinate axes and the lower left corner located on the straight line at a certain "cutoff" value of the Carbo score (see FIG. 15A). In what follows, all points falling into that rectangle are considered to be hits of the database query. FIG. 15B shows the percentage of hits relative to the size of the diversity set (continuous line) as well as relative to the number of DHFR inhibitors (broken line) as a function of the Carbo score cutoff parameter. This illustrates the balance of selectivity and sensitivity, i.e., the signal-to-noise ratio of the similarity search method. The lines in this plot may be interpreted as false positives (diversity set) and true positives (DHFR inhibitors). It is seen that if 50% of the DHFR inhibitors are found (50% false negatives at a Carbo score cutoff value of 0.69), then there are also about 3% false positives. FIG. 15C shows an ROC (receiver-operator curve) plotting the true vs. the false positive hits.

2.4 Architecture

Figure 17:
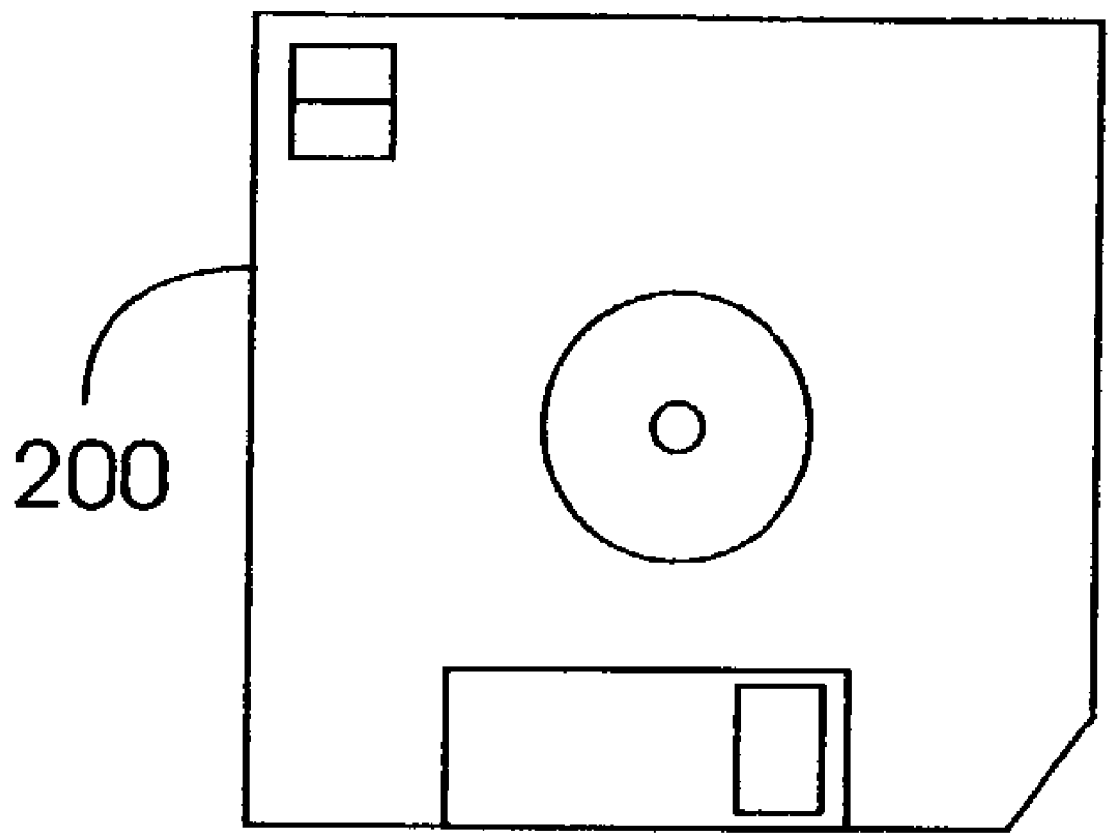
FIG. 17 shows a computer program product for storing executable program code that may be used in implementing the methods disclosed herein.

In preferred embodiments of the invention, there is provided media encoded with executable program code to effect any of the methods described herein. This code contains executable instructions that may reside, for example, in the random access memory (RAM) of a processor, or on a hard drive or optical drive of a processor. The instructions may be stored on a magnetic or optical disk or diskette, a disk drive, magnetic tape, electronic read-only memory, or other appropriate data storage device. For example, see the computer program product 200 shown in FIG. 17. In preferred embodiments, this program code may be read by a digital processing apparatus such as a processor or computer for performing any one or more of the methods disclosed herein.

Figure 18:
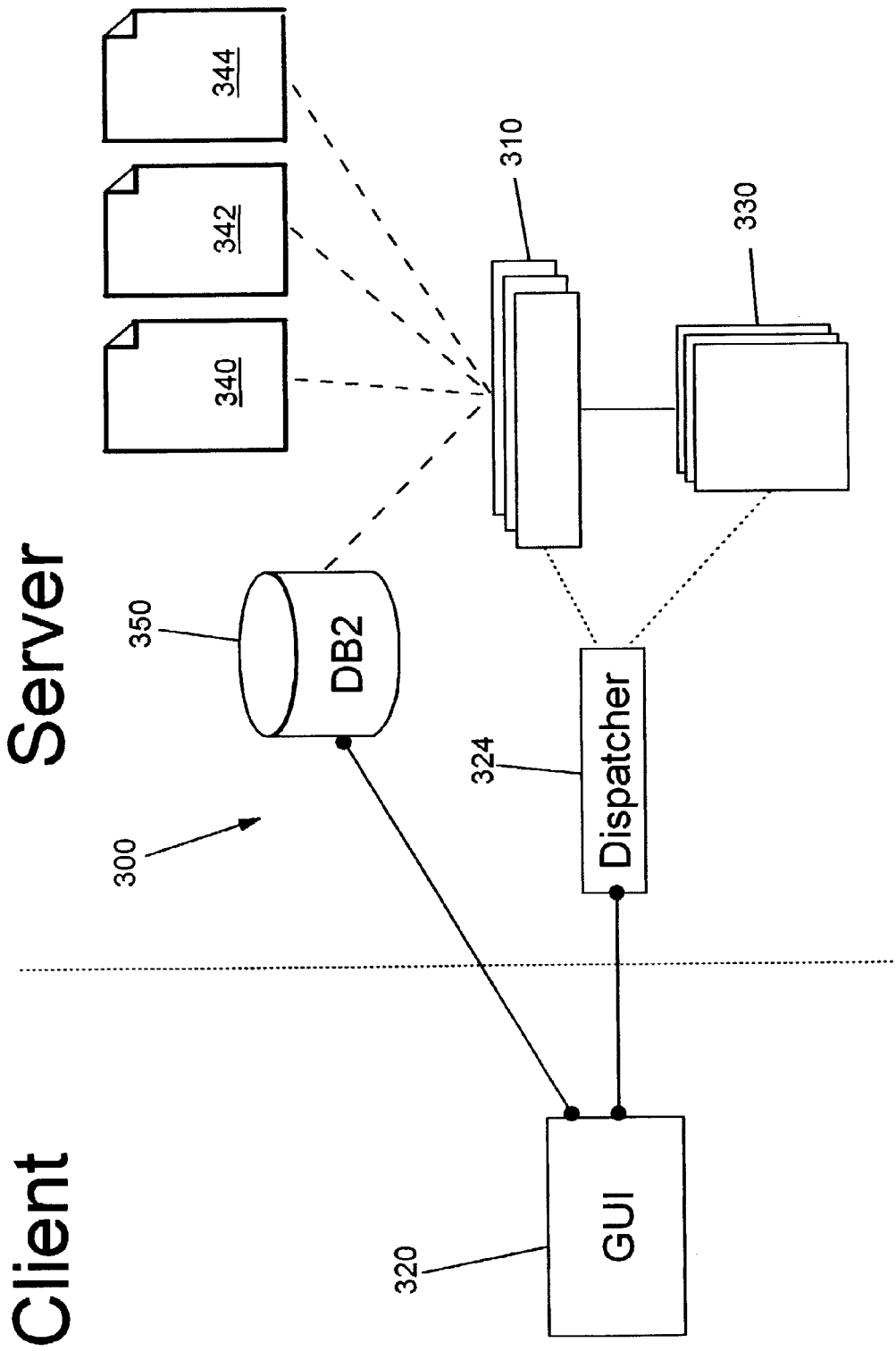
FIG. 18 shows an overview of the architecture used in preferred implementations of the methods disclosed herein.

Preferred computer architecture is now discussed in connection with FIG. 18, which shows client 320/server 300 architecture. The server 300 includes a request dispatcher 324 written in Java, the applications 310 (implemented in C++ and including the query engine), UNIX shell scripts 330, a compound database 340 on flat files, a conformational database 342 on flat files, a feature database 344 on flat files, and a DB2 database 350 for keeping track of query results and the files in the compound, conformational, and feature databases. The server components run on AIX. The components of the server 300 run on an IBM RS/6000 workstation.

The client 320 includes a graphical user interface ("GUI", implemented in Java) that is run on a personal computer, such as a Win32 PC. The graphical user interface of the client 320 is used to populate databases, to issue queries, and to visualize results. Alternatively the client and server can be installed on a stand-alone PC or laptop.

The communication protocol between the client 320 and the database 350 is JDBC/SQL, and the protocol between the client 320 and the dispatcher 324 is ASCII streams over TCP/IP sockets. The dispatcher 324 issues requests to the applications 310 and the shell scripts 330 using system calls, and the applications 310 communicate with the database 350 using CLI/SQL.

2.5 Software Workflow

Figure 19:
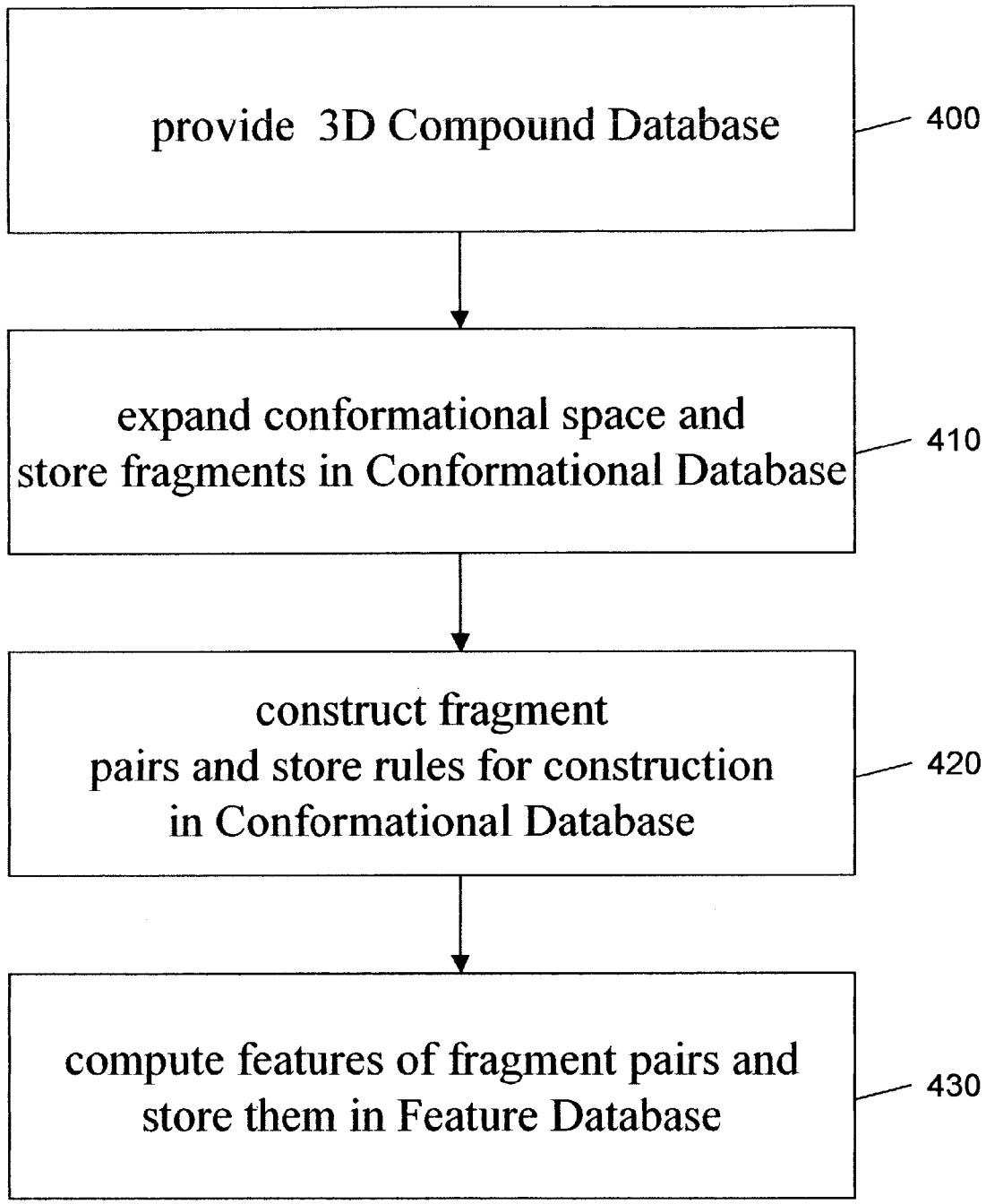
FIG. 19 outlines the steps involved in a preferred database preprocessing method.

A preferred preprocessing methodology is shown in FIG. 19. In step 400, the user provides a database of 3-D compounds. For each of the molecules in the 3-D compound database, the conformation space is expanded, and fragments and fragment pairs are generated (step 410). These fragments and the rules for the fragment pairs are then stored in a conformational database (step 420). For each of fragment pairs in the conformational database, features are computed and stored in a feature database (step 430).

Figure 20:
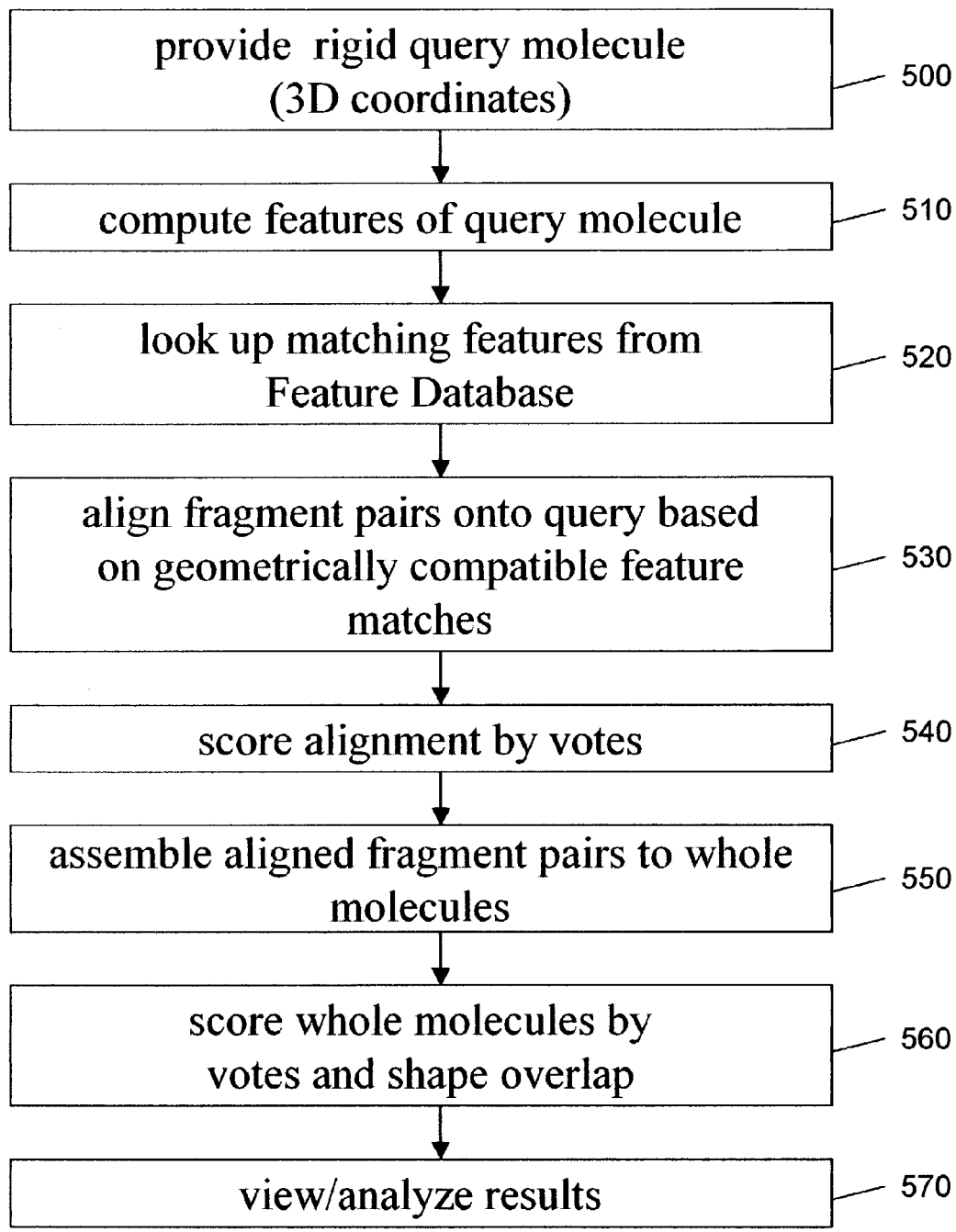
FIG. 20 outlines the steps involved in a preferred query method.

A preferred query methodology is outlined in FIG. 20. The user provides 3-D coordinates of a query molecule (step 500). The features of the query molecule are computed (step 510), and for each of the query features, matching fragment pair features are looked up from the feature database (step 520). Alignments of fragment pairs onto the query molecule are computed based on geometrically compatible feature matches (step 530), and these alignments are scored by votes (step 540). Aligned fragment pairs are assembled into whole molecules (step 550), and the whole molecules are scored by votes and shape overlap (step 560). The resultant whole molecules are viewed and analyzed (step 570).

3.0 Discussion

Although the methods herein are described with respect to a linear chain-like fragmentation approach which generally seems to be sufficient for medium-sized, drug-like molecules, the methods may be more generally used to handle closures of large ring structures, and, more importantly, be applied to branched molecules. In section 2.2, the issue of asymmetry between query and database molecules with respect to their size was discussed. This asymmetry can be reduced by allowing for the assembly of partial candidates and appending the missing fragment "tails" in an arbitrary conformation. Likewise, the sensitivity of the method can be increased by bridging gaps within a candidate if certain fragment pairs do not get enough support in the pattern matching procedure.

In other preferred methods of the invention, the user may actively manipulate features on the query molecule by introducing weights, or switching features on and off entirely according to their importance in the receptor-ligand interaction, e.g., with the aid of a monitor on which molecules and features are displayed. This way, the user may distinguish between parts of the query molecule that are solvent-exposed, and parts that bind to the protein. The resulting molecular alignments can be still further improved in a post-processing step by relaxing the conformational constraints and performing a continuous optimization of the RMSD of feature matches, i.e., the final alignments may be still further improved through the post-processing of candidates. In still other preferred methods, a receptor model instead of a single conformation of a query molecule may be used in order to allow for docking-type applications (see, for example, J. S. Mason et al., J. Med. Chem., vol. 42, p. 3251, 1999; and J. E. Eksterowicz et al., J. Mol. Graphics Modeling, vol. 20, p. 469, 2002).

Methods have been presented herein that make use of relatively simple, atom type based feature definition, resulting in good results for the set of medium-sized drug-like molecules considered herein. In addition, tests with larger molecules (HIV protease inhibitors) performed with the benchmark FlexS-77 dataset collected by C. Lemmen et al. (see the Interent website identified by the concatenation of "http://" and "www.biosolveit.de" and J. Med. Chem., vol. 41, p. 4502, 1998) found correct alignments in some cases; however, local shape similarity, e.g., the packing of hydrophobic sidechains, plays an important role for these structures, which is not properly resolved in the atom-based feature definition presented here. This suggests that other, more appropriate feature schemes, which also encode local shape properties, should be used in those situations. This is, in principle, possible since features are explicitly allowed to depend on fragment pair conformations, a capability used in the "geometric" definition of hydrophobic regions.

A feature scheme that distinguishes between (atom type-based) features in a locally or non-flat environment may be constructed. This increases the selectivity of the molecular similarity search method, since there is now a larger set of feature indices, and therefore fewer feature correspondences. A convenient side effect is that query-processing times are reduced by a factor of 2-3, because the workload for the clique detection algorithm is smaller. Using this feature scheme, it was possible to reproduce all but 4 alignments reported in FIG. 10; in addition, results qualitatively similar to those shown in FIG. 15 when querying dihydrofolate against our test database were obtained.

The invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes within the meaning and range of equivalency of the claims are to be embraced within that scope.

What is claimed is:

1. A computer-implemented method of identifying at least a portion of a molecule indexed in a database, the molecule having both a conformation and at least one physico-chemical property similar to those of a query molecule, the database including at least one conformation representation for each of a plurality of indexed molecules, wherein each of the indexed molecules is partitioned into a set of overlapping fragments, and in which at least one conformation representation is associated with each fragment, and in which for each of the fragment conformation representations, at least 3 computed features of interest of the fragment have been provided, each of said at least 3 computed features corresponding to a different, single point in 3-D physical space and representing at least one given physico-chemical property, the method comprising:

a) providing a conformation of a query molecule that includes at least 3 computed features, each of which corresponding to a different, single point in 3-D physical space and corresponds to at least one physico-chemical property of interest, wherein at least one of the computed features of the query molecule is not located at an atomic site;

b) using a computer for pattern matching said at least 3 computed features of the query molecule with corresponding computed features of fragments given by fragment conformation representations in the database to identify fragments having patterns of computed features similar to patterns of computed features in portions of the query molecule, wherein said pattern matching includes i) first matching just feature type and ii) then matching feature geometry;

c) using a computer for assembling geometrically compatible overlapping fragment conformations corresponding to fragments identified by said pattern matching into at least one three-dimensional molecular structure that corresponds to at least a portion of at least one of the indexed molecules, in order to identify at least a portion of a molecule in the database having patterns of computed features similar to patterns of computed features in the query molecule; and d) using a computer to present, to a user, results generated by steps a), b), and c), so that the user is able to view and analyze the results.

2. The method of claim 1, wherein said three-dimensional molecular structure corresponds to at least one entire indexed molecule.

3. The method of claim 2, further comprising, for each one of the overlapping fragments, calculating a set of conformations by sampling torsional angles corresponding to rotatable bonds of said one of the overlapping fragments.

4. The method of claim 2, further comprising using a graph-based algorithm for at least one of said pattern matching and said assembling.

5. The method of claim 2, wherein said fragment conformations include conformations corresponding to fragments that have at least 20 atoms.

6. The method of claim 2, wherein said overlapping fragments are constructed from pairs of adjacent non-overlapping fragments separated by one rotatable bond.

7. The method of claim 6, wherein said assembling is based on the detection of directed paths in a directed graph having vertices representing the adjacent non-overlapping fragments.

8. The method of claim 7, wherein said assembling includes scoring of said three-dimensional molecular structures without using their three-dimensional coordinates.

9. The method of claim 2, wherein conformations corresponding to the conformation representations associated with the fragments are selected by avoiding processing two or more overlapping fragment conformations during a database query if those overlapping fragment conformations are not sufficiently distinct from each other by a predetermined measure.

10. The method of claim 2, said pattern matching including identifying feature pairs, wherein each feature pair includes a computed feature in the query molecule and a corresponding computed feature in a database molecule.

11. The method of claim 2, wherein said pattern matching is based on clique-detection in a distance-compatibility graph.

12. The method of claim 11, wherein said pattern matching does not require knowledge of local coordinate systems.

13. The method of claim 2, wherein said computed features of the fragments represent at least one of the following physico-chemical properties: hydrogen bond donors, hydrogen bond acceptors, hydrophobic regions, aromatic rings, acid groups, and base groups.

14. The method of claim 2, further comprising partitioning the indexed molecules by an automated procedure using an algorithm that minimizes the number of conformations to be stored in the database.

15. The method of claim 2, further comprising populating the database with the indexed molecules and their respective overlapping fragments and computed features.

16. The method of claim 2, said matching of feature geometry including:
   i) determining that distances between computed features of the query molecule and distances between corresponding computed features of a pair of adjacent fragments given by fragment conformation representations in the database are within a predetermined tolerance, and
   ii) determining that pairs of computed features of the query molecule and corresponding pairs of computed features of said pair of adjacent fragments can be aligned to within a predetermined angular tolerance.

17. The method of claim 1, wherein said matching of feature geometry includes a distance tolerance determination between computed features of the query molecule and computed features of a pair of adjacent fragments given by fragment conformation representations in the database.

18. The method of claim 17, wherein said matching of feature geometry includes an angular tolerance determination between computed features of the query molecule and computed features of a pair of adjacent fragments given by fragment conformation representations in the database.

19. The method of claim 1, wherein:
   matching computed features are grouped into sets based on geometrical considerations, each of these sets defining a respective unique alignment of a fragment onto the query molecule, and
   fragments identified by said pattern matching are identified by said respective alignments.

20. The method of claim 1, wherein said fragment conformations include conformations corresponding to fragments that have at least 20 atoms.

21. The method of claim 1, wherein at least one computed feature of the query molecule corresponds to an aromatic ring.

22. The method of claim 1, wherein at least one computed feature of the query molecule: i) corresponds to a benzene ring and ii) is associated with a point at the center of the benzene ring.

23. The method of claim 1, wherein at least one computed feature of the query molecule: i) corresponds to a hydrophobic group and ii) is associated with a point at the hydrophobic group's center of geometry.

24. A product comprising a computer-readable medium that tangibly embodies a computer executable program thereon, the program designed for identifying at least a portion of a molecule indexed in a database, the molecule having both a conformation and at least one physico-chemical property similar to those of a query molecule provided by a user of the program, the database including at least one conformation representation of each of the indexed molecules, wherein each of the indexed molecules is partitioned into a set of overlapping fragments, and in which at least one conformation representation is associated with each fragment, and in which for each of the fragment conformation representations, at least 3 computed features of interest of the fragment have been provided, each of said at least 3 computed features corresponding to a different, single point in 3-D physical space and representing at least one given physico-chemical property, the program having instructions that cause a computer to implement the following steps when the program is executed on the computer, in response to a user of the program providing a conformation of the query molecule that includes at least 3 computed features, each of which corresponds to a different, single point in 3-D physical space and corresponds to at least one physico-chemical property of interest:

a) pattern matching said at least 3 computed features of the query molecule with corresponding computed features of fragments given by fragment conformation representations in the database to identify fragments having patterns of computed features similar to patterns of computed features in portions of the query molecule, wherein said pattern matching includes i) first matching just feature type and ii) then matching feature geometry; and b) assembling geometrically compatible overlapping fragment conformations corresponding to fragments identified by said pattern matching into at least one three-dimensional molecular structure that corresponds to at least a portion of at least one of the indexed molecules, in order to identify at least a portion of a molecule in the database having patterns of computed features similar to patterns of computed features in the query molecule, wherein at least one of the computed features of the query molecule is not located at an atomic site.

25. The product of claim 24, wherein said three-dimensional molecular structure corresponds to at least one entire indexed molecule.

26. The product of claim 25, wherein said pattern matching is based on clique-detection in a distance-compatibility graph.

27. The product of claim 25, said matching of feature geometry including:
i) determining that distances between computed features of the query molecule and distances between corresponding computed features of a pair of adjacent fragments given by fragment conformation representations in the database are within a predetermined tolerance, and
ii) determining that pairs of computed features of the query molecule and corresponding pairs of computed features of said pair of adjacent fragments can be aligned to within a predetermined angular tolerance.

28. The product of claim 25, wherein at least one computed feature of the query molecule: i) corresponds to a benzene ring and ii) is associated with a point at the center of the benzene ring.

29. The product of claim 24, wherein said matching of feature geometry includes a distance tolerance determination between computed features of the query molecule and computed features of a pair of adjacent fragments given by fragment conformation representations in the database.

30. The product of claim 29, wherein said matching of feature geometry includes an angular tolerance determination between computed features of the query molecule and computed features of a pair of adjacent fragments given by fragment conformation representations in the database.

31. The product of claim 24, wherein:
matching computed features are grouped into sets based on geometrical considerations, each of these sets defining a respective unique alignment of a fragment onto the query molecule, and
fragments identified by said pattern matching are identified by said respective alignments.

32. The product of claim 24, wherein conformations corresponding to the conformation representations associated with the fragments are selected by avoiding processing two or more overlapping fragment conformations during a database query if those overlapping fragment conformations are not sufficiently distinct from each other by a predetermined measure.

33. The product of claim 24, the program further including instructions for:
using the computer to present, to a user, results generated by steps a) and b).

34. A computer-implemented method of identifying at least a portion of a molecule indexed in a database, the molecule having both a conformation and at least one physico-chemical property similar to those of a query molecule, the database including at least one conformation representation of each of the indexed molecules, wherein each of the indexed molecules is partitioned into a set of overlapping fragments, and in which at least one conformation representation is associated with each fragment, and in which for each of the fragment conformation representations, at least 3 computed features of interest of the fragment have been provided, each of said at least 3 computed features corresponding to a different, single point in 3-D physical space and representing at least one given physico-chemical property, the method comprising:

a) providing a conformation of a query molecule that includes at least 3 computed features, each of which corresponds to a different, single point in 3-D physical space and corresponds to at least one physico-chemical property of interest;

b) using a computer for pattern matching said at least 3 computed features of the query molecule with corresponding computed features of fragments given by fragment conformation representations in the database to identify fragments having patterns of computed features similar to patterns of computed features in portions of the query molecule, wherein said pattern matching includes i) first matching just feature type and ii) then matching feature geometry;

c) using a computer for assembling geometrically compatible overlapping fragment conformations corresponding to fragments identified by said pattern matching into at least one three-dimensional molecular structure that corresponds to at least a portion of at least one of the indexed molecules, in order to identify at least a portion of a molecule in the database having patterns of computed features similar to patterns of computed features in the query molecule, wherein conformations corresponding to the conformation representations associated with the fragments are selected by avoiding processing two or more overlapping fragment conformations during a database query if those overlapping fragment conformations are not sufficiently distinct from each other by a predetermined measure; and d) using a computer to present, to a user, results generated by steps a), b), and c), so that the user is able to view and analyze the results.

35. The method of claim 34, wherein said three-dimensional molecular structure corresponds to at least one entire indexed molecule.

36. A product comprising a computer-readable medium that tangibly embodies a computer executable program thereon, the program designed for identifying at least a portion of a molecule indexed in a database, the molecule having both a conformation and at least one physico-chemical property similar to those of a query molecule provided by a user of the program, the database including at least one conformation representation of each of the indexed molecules, wherein each of the indexed molecules is partitioned into a set of overlapping fragments, and in which at least one conformation representation is associated with each fragment, and in which for each of the fragment conformation representations, at least 3 computed features of interest of the fragment have been provided, each of said at least 3 computed features corresponding to a different, single point in 3-D physical space and representing at least one given physico-chemical property, the program having instructions that cause a computer to implement the following steps when the program is executed on the computer, in response to a user of the program providing a conformation of the query molecule that includes at least 3 computed features, each of which corresponds to a different, single point in 3-D physical space and corresponds to at least one physico-chemical property of interest:

a) pattern matching said at least 3 computed features of the query molecule with corresponding computed features of fragments given by fragment conformation representations in the database to identify fragments having patterns of computed features similar to patterns of computed features in portions of the query molecule, wherein said pattern matching includes i) first matching just feature type and ii) then matching feature geometry; and b) assembling geometrically compatible overlapping fragment conformations corresponding to fragments identified by said pattern matching into at least one three-dimensional molecular structure that corresponds to at least a portion of at least one of the indexed molecules, in order to identify at least a portion of a molecule in the database having patterns of computed features similar to patterns of computed features in the query molecule, wherein conformations corresponding to the conformation representations associated with the fragments are selected by avoiding processing two or more overlapping fragment conformations during a database query if those overlapping fragment conformations are not sufficiently distinct from each other by a predetermined measure.

37. The product of claim 36, wherein said three-dimensional molecular structure corresponds to at least one entire indexed molecule.

38. The product of claim 36, the program further including instructions for:

using the computer to present, to a user, results generated by steps a) and b).

* * * * *